United States Patent
Buchardt et al.

(10) Patent No.: US 9,234,192 B2
(45) Date of Patent: Jan. 12, 2016

(54) CONJUGATED PROTEINS

(75) Inventors: Jens Buchardt, Gentofte (DK); Carsten Behrens, Copenhagen N (DK)

(73) Assignee: Novo Nordisk A/S, Bagvaerd (DK)

( * ) Notice: Subject to any disclaimer, the term of this patent is extended or adjusted under 35 U.S.C. 154(b) by 0 days.

(21) Appl. No.: 13/575,207

(22) PCT Filed: Feb. 9, 2011

(86) PCT No.: PCT/EP2011/051889
§ 371 (c)(1),
(2), (4) Date: Sep. 11, 2012

(87) PCT Pub. No.: WO2011/101277
PCT Pub. Date: Aug. 25, 2011

(65) Prior Publication Data
US 2013/0004524 A1    Jan. 3, 2013

Related U.S. Application Data

(60) Provisional application No. 61/305,723, filed on Feb. 18, 2010.

(30) Foreign Application Priority Data

Feb. 16, 2010    (EP) .................................. 10153716

(51) Int. Cl.
| A61K 38/16 | (2006.01) |
| A61P 29/00 | (2006.01) |
| A61P 7/04 | (2006.01) |
| C12N 9/64 | (2006.01) |
| A61K 47/14 | (2006.01) |
| C07K 14/745 | (2006.01) |
| C07K 14/755 | (2006.01) |

(52) U.S. Cl.
CPC ............... *C12N 9/644* (2013.01); *A61K 47/14* (2013.01); *C07K 14/745* (2013.01); *C07K 14/755* (2013.01); *C12N 9/6437* (2013.01); *C12Y 304/21021* (2013.01); *C12Y 304/21022* (2013.01)

(58) Field of Classification Search
None
See application file for complete search history.

(56) References Cited

U.S. PATENT DOCUMENTS

| 2005/0250678 | A1 | 11/2005 | DeFrees et al. |
| 2007/0105755 | A1 | 5/2007 | DeFrees et al. |
| 2008/0146782 | A1 | 6/2008 | DeFrees et al. |
| 2008/0280818 | A1 | 11/2008 | DeFrees |
| 2009/0028822 | A1 | 1/2009 | DeFrees et al. |
| 2012/0093840 | A1 * | 4/2012 | Ostergaard et al. ........ 424/178.1 |

FOREIGN PATENT DOCUMENTS

| DE | 4437604 A1 | 4/1996 |
| JP | 2004141173 A | 5/2004 |
| WO | 2004/000366 A1 | 12/2003 |
| WO | 2006/010143 A2 | 1/2006 |
| WO | 2006/035057 A1 | 4/2006 |
| WO | 2006/066258 A2 | 6/2006 |
| WO | 2008/025856 A2 | 3/2008 |
| WO | 2008/124406 A2 | 10/2008 |
| WO | 2008/151258 A2 | 12/2008 |
| WO | 2009/058446 A1 | 5/2009 |
| WO | 2009/089396 | 7/2009 |
| WO | 2009/108806 A1 | 9/2009 |
| WO | 2009/156137 A1 | 12/2009 |
| WO | 2010/115866 A1 | 10/2010 |

OTHER PUBLICATIONS anonymus—dated Apr. 22, 2009—XP007918608, Sialic Acid, from: http://replay.web.archive.org/20090422161857/.

* cited by examiner

*Primary Examiner* — Brian J Gangle
*Assistant Examiner* — Andrea McCollum
(74) *Attorney, Agent, or Firm* — Nonna G. Akopyan

(57) ABSTRACT

The present invention relates to modified therapeutic proteins, such as e.g. coagulation factors. In particular, the present invention relates to conjugated Factor VIII molecules such as e.g. FVII, FVIII, or FIX comprising a hydrophobic side group.

14 Claims, No Drawings

CONJUGATED PROTEINS

CROSS-REFERENCE TO RELATED APPLICATIONS

This application is a 35 U.S.C. §371 national stage application of International Patent Application PCT/EP2011/051889 (published as WO 2011/101277), filed Feb. 9, 2011, which claimed priority of European Patent Application 10153716.5, filed Feb. 16, 2010; this application further claims priority under 35 U.S.C. §119 of U.S. Provisional Application 61/305,723, filed Feb. 18, 2010.

FIELD OF THE INVENTION

The present invention relates to modified proteins. In particular, the present invention relates to proteins such as e.g. coagulation factors conjugated with a hydrophobic side group. The invention furthermore relates to use of such molecules as well as methods for producing such molecules.

BACKGROUND OF THE INVENTION

Haemophilia A is an inherited bleeding disorder caused by deficiency or dysfunction of coagulation factor VIII (FVIII) activity. The clinical manifestation is not on primary haemostasis—formation of the blood clot occurs normally—but the clot is unstable due to a lack of secondary thrombin formation. The disease is treated by intravenous injection of coagulation factor FVIII which is either isolated from blood or produced recombinantly. Haemophilia A patients with inhibitors may be treated by on-demand administration of factor VIIa (FVIIa). Haemophilia B is caused by deficiency or dysfunction of coagulation factor IX (FIX) activity and patients can be treated by on demand administration of factor IX (FIX).

Current treatment recommendations are moving from traditional on-demand treatment towards prophylaxis. The circulatory half life of endogenous FVIII bound to von Willebrandt Factor is 12-14 hours and prophylactic treatment is thus to be performed several times a week in order to obtain a virtually symptom-free life for the patients. Circulatory half life of endogenous factor VII is less than 2 hours. Circulatory half life of endogenous factor IX is 19-24 hours. I.V. administration is for many, especially children and young persons, associated with significant inconvenience and/or pain. There is thus a need in the art for prolonging the circulatory half life of recombinant coagulation factors. There is likewise a need in the art for prolonging the half life of a number of other therapeutic proteins and peptides in a site-directed manner preferably resulting in a relatively homogenous and well defined product.

Various methods have been employed in the development of coagulation factors, and of pharmaceutical proteins in general, with significantly prolonged circulatory half life. A number of these methods relate to conjugation with hydrophilic polymers such as e.g. PEG (poly ethylene glycol). Conjugation with hydrophobic side chains do on the one hand constitute an attractive approach due to the fact that such groups might be completely degraded in vivo. On the other hand, conjugation of proteins with one or more well-defined hydrophobic moieties has so far not constituted an attractive approach for half-life prolongation of relatively large proteins, including coagulation factors such as e.g. FVIII. In fact, conjugation of such hydrophobic moieties to proteins would not be considered a realistic approach due to: 1) large proteins such as FVIII are only stable in aqueous buffers devoid of organic solvents; 2) lipophilic moieties such as fatty acids are insoluble in such aqueous buffers; 3) it would be doubtful that attachment of relatively small lipophilic moieties would result in any significant protraction of much larger proteins such as e.g. FVIII; 4) lipophilic moieties, when attached to the normally hydrophilic surface of proteins, may pertube their stability due to aggregation or energetically favorable but destructive unfolding; and 5) interaction of the protein with its natural binding partners may be pertubed in similar way leading to reduced biological activity.

SUMMARY OF THE INVENTION

The present invention relates to recombinant protein molecules, such as e.g. antigen binding fragments of antibodies, FVII, FVIII, and FIX, wherein said protein molecules are covalently conjugated to at least one hydrophobic side group via a sialic acid. The invention furthermore relates to methods for making such conjugates as well as use of such conjugates.

Such conjugates have a modified circulatory half life and do preferably have a relatively homogenous structure. The conjugates furthermore retain biological activity and are preferably produced without using any organic solvents. It is, however, possible to employ a method for making such molecules wherein said method comprises use of trace amounts of organic solvents.

DESCRIPTION OF THE INVENTION

Definitions:

Proteins

Proteins and peptides within the scope of the invention are preferably proteins/peptides suitable for therapeutic treatment. Such proteins include, but are not limited to serum proteins such as blood coagulation coagulation factors, hemoglobin, immunoglobulins, antibodies, antigen binding fragments of antibodies such as e.g. Fab fragments, cytokines such as interleukins, alpha-, beta-, and gamma-interferons, members of the TNF-receptor family such as e.g. DR3, TNF1R, TNF2R, CD27 and CD30, colony stimulating factors including granulocyte colony stimulating factors, platelet derived growth factors and phospholipase-activating protein (PUP). Other proteins include insulin, GLP-1, GLP-2, plant proteins such as lectins and ricins, tumor necrosis factors and related alleles, soluble forms of tumor necrosis factor receptors, interleukin receptors and soluble forms of interleukin receptors, human growth hormone, growth factors such as tissue growth factors, such as TGFa's or TGFps and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE. IgM. IgA, IgD and fragments thereof.

The protein according to the invention may be structurally similar to the native protein and may be derived from the native protein by addition of one or more amino acids to either or both the C and N-terminal end of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence.

The term "antibody", "monoclonal antibody" and "mAb" as used herein, is intended to refer to immunoglobulin molecules and fragments thereof that have the ability to specifically bind to an antigen. Full-length antibodies comprise four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. A full-length antibody is normally bi-valent/di-valent, i.e. it has the capacity to bind to the antigen with both "arms". In contrast, a mono-valent antibody according to the present invention comprises only one binding site specific for the antigen.

The "Fab region"/"Fab domain"/" Fab fragment, contains variable sections that define the specific target that the antibody can bind. A Fab fragment is an example of a monospecific/mono-valent antibody according to the present invention. Conjugated Fab fragments according to the present invention often have a significantly increased circulatory half life compared to Fab fragments that have not been post-translationally modified. Fab fragments and other antigen binding fragments of antibodies are thus particularly useful in modulation of the immune system and thus treatment of e.g. cancer and immune related disorders, such as e.g. auto-inflammatory disesases (including psoriasis, type I diabetes, Grave's disease, Inflammatory bowel disease (IBD), Crohn's disease, ulcerative colitis, irritable bowel syndrome, multiple sclerosis, rheumatoid arthritis (RA), autoimmune myocarditis, Kawasaki disease, coronary artery disease, chronic obstructive pulmonary disease, interstitial lung disease, autoimmune thyroiditis, systemic lupus erythematosus (SLE), *scleroderma*, systemic sclerosis, psoriatic arthritis, osteoarthritis, atoptic dermatitis, vitiligo, graft vs. host disease, Sjöogrens's syndrome, autoimmune nephritis, Goodpasture's syndrome, chronic inflammatory demyeliniating polyneutopathy, allergy, asthma and other autoimmune diseases).

Examples of mono-valent antibodies according to the present invention include: Fab fragments, monovalent fragments consisting of the VL, VH, CL and CH I domains; a bivalent fragment comprising two Fab fragments linked e.g. by a disulfide bridge at the hinge region, where only one of these Fab fragments is specific for its antigen; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; (vi) an isolated complementarity determining region (CDR); and (v) a bi-specific antibody that is monovalent for its antigen.

Coagulation factors: Coagulation factors are involved in formation of the secondary clot. The coagulation factors include the following: vWF, factor I, factor II (prothrombin), factor V, factor VII, factor VIII, factor IX, factor X, factor XI, factor XII, and factor XIII. Coagulation factor variants according to the present invention have coagulation factor activity, i.e., the activity of the molecules is at least 25% of the native coagulation factor activity, preferably at least 50%, more preferably at least 75%, and most preferably at least 90% of native coagulation factor activity.

Factor VII (FVII) is a glycoprotein primarily produced in the liver. The mature protein consists of 406 amino acid residues and is composed of four domains as defined by homology. There is an N-terminal Gla domain followed by two epidermal growth factor (EGF)-like domains and a C-terminal serine protease domain. FVII circulates in plasma as a single-chain molecule. Upon activation to activated FVII (FVIIa), the molecule is cleaved between residues Arg152 and Ile153, resulting in a two-chain protein held together by a disulphide bond. The light chain contains the Gla and EGF-like domains, whereas the heavy chain is the protease domain. FVIIa requires binding to its cell-surface cofactor tissue factor to become biologically active.

Factor VII(a) may be plasma-derived or recombinantly produced, using well known methods of production and purification. The degree and location of glycosylation, gamma-carboxylation and other post-translational modifications may vary depending on the chosen host cell and its growth conditions. The term "Factor VII polypeptide" may refer to the zymogen as well as the activated form of Factor VII. The term "Factor VII(a) polypeptide" herein refers to wild type Factor VIIa molecules as well as FVII(a) variants, FVII(a) derivatives and FVII(a) conjugates. Such variants, derivatives and conjugates may exhibit substantially the same, or improved, biological activity relative to wild-type human Factor VIIa.

"FVII/FVII variants" according to the present invention comprises Factor FVII having the sequence of SEQ ID NO:1, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein.

FVII variants furthermore comprise a FVII polypeptide that exhibits substantially the same or improved biological activity relative to wild-type Factor VIIa, in which one or more of the amino acids of the parent peptide have been genetically and/or chemically and/or enzymatically modified, such as by alkylation, glycosylation, PEGylation, acylation, ester formation, disulfide bond formation, or amide formation.

```
SEQ ID NO. 1:
Wild type human coagulation Factor VII
ANAFLγγLRPGSLγRγCKγγQCSFγγARγIFKDAγRTKLFWISYSDGDQ

CASSPCQNGGSCKDQLQSYICFCLPAFEGRNCETHKDDQLICVNENGGC

EQYCSDHTGTKRSCRCHEGYSLLADGVSCTPTVEYPCGKIPILEKRNAS

KPQGRIVGGKVCPKGECPWQVLLLVNGAQLCGGTLINTIWVVSAAHCFD

KIKNWRNLIAVLGEHDLSEHDGDEQSRRVAQVIIPSTYVPGTTNHDIAL

LRLHQPVVLTDHVVPLCLPERTFSERTLAFVRFSLVSGWGQLLDRGATA

LELMVLNVPRLMTQDCLQQSRKVGDSPNITEYMFCAGYSDGSKDSCKGD

SGGPHATHYRGTWYLTGIVSWGQGCATVGHFGVYTRVSQYIEWLQKLMR

SEPRPGVLLRAPFP
```

γ: Represents gamma-carboxylated Glu ('E') residues.
FVIIa conjugate activity may be determined as follows:

Prothrombin and FX are treated with a mixture of inhibitors to neutralize traces of active enzymes. FX (135 nM final concentration), prothrombin (1.2 uM), TF pathway inhibitor (0.1 ug/ml), and antithrombin (AT, 2.5 uM) are mixed with CaCl2 (3 mM) and stored over night at 4° C. Peripheral blood from healthy volunteers is drawn into citrate. Platelets are isolated by density gradient centrifugation and gel filtration as described in M. Kjalke *Thromb. Heamostasis* 78, 1202-1208, 1997 and activated by incubation with 50 ug/ml thrombin receptor agonist peptide (SFLLRN) for 15 min at 37° C. An aliquot of the platelet suspension is transferred to Tru-Count tubes (Becton Dickinson), and the platelet density is determined by using fluorescent beads as the standard on a FACScan flow cytometer (Becton Dickinson) as described by the manufacturer. A final platelet density of approximately 100,000/ul is used. Factor V (final concentration 7 ug/ml) is added to the protein/Ca2+ mixture. FVIIa conjugates (50 nM) is then added, followed by platelets, to give a final volume of 200 ul. At timed intervals, aliquots of 10 ul is transferred to 90 ul of 0.5 mM Chromozym TH (Roche Molecular Biochemicals) in 20 mM Hepes, pH 7.4, containing 150 mM NaCl, 1 mg/ml BSA, 1 mM EDTA, and 50 uM Pefabloc Xa (Pentapharm, Basel). Substrate hydrolysis is stopped after 20 min by adding 100 ul of 50% acetic acid, and the absorbance at 405 nm is measured. The thrombin concentration is calculated from a thrombin standard curve. Further assays for characterizing FVIIa activity may be found in WO 07031559 or Person, *PNAS* 98(24) 13583-13588, 2001 and references cited herein.

Factor VIII molecules: FVIII/Factor VIII is a large, complex glycoprotein that primarily is produced by hepatocytes. FVIII consists of 2351 amino acids, including signal peptide, and contains several distinct domains, as defined by homology. There are three A-domains, a unique B-domain, and two C-domains. The domain order can be listed as NH2-A1-A2-B-A3-C1-C2-COOH. FVIII circulates in plasma as two chains, separated at the B-A3 border. The chains are connected by bivalent metal ion-bindings. The A1-A2-B chain is termed the heavy chain (HC) while the A3-C1-C2 is termed the light chain (LC).

Endogenous Factor VIII molecules circulate in vivo as a pool of molecules with B domains of various sizes. What probably occurs in vivo is a gradual enzymatic removal of the B domain resulting in a pool of molecules with B-domains of various sizes. It is generally believed that cleavage at position 740, by which the last part of the B-domain is removed, occurs in connection with thrombin activation. However, it cannot be ruled out that a Factor VIII variant in which e.g. the cleavage site at position 740 has been impaired may be active.

"Factor VIII" or "FVIII" as used herein refers to a human plasma glycoprotein that is a member of the intrinsic coagulation pathway and is essential to blood coagulation. "Native FVIII" is the full length human FVIII molecule as shown in SEQ ID NO. 2 (amino acid 1-2332). The B-domain is spanning amino acids 741-1648 in SEQ ID NO 2.

SEQ ID NO 2:
ATRRYYLGAVELSWDYMQSDLGELPVDARFPPRVPKSFPFNTS
DVVYKKTLFVEFTHLFNIAKPRPPWMGLLGPTIQAEVYDTVVITLKNMA
SHPVSLHAVGVSYWKASEGAEYDDQTSQREKEDDKVFPGGSHTYVWQVL
KENGPMASDPLCLTYSYLSHVDLVKDLNSGLIGALLVCREGSLAKEKTQ
TLHKFILLFAVFDEGKSWHSETKNSLMQDRDAASARAWPKMHTVNGYVN
RSLPGLIGCHRKSVYWHVIGMGTTPEVHSIFLEGHTFLVRNHRQASLEI
SPITFLTAQTLLMDLGQFLLFCHISSHQHDGMEAYVKVDSCPEEPQLRM
KNNEEAEDYDDDLTDSEMDVVRFDDDNSPSFIQIRSVAKKHPKTWVHYI

-continued
AAEEEDWDYAPLVLAPDDRSYKSQYLNNGPQRIGRKYKKVRFMAYTDET
FKTREAIQHESGILGPLLYGEVGDTLLIIFKNQASRPYNIYPHGITDVR
PLYSRRLPKGVKHLKDFPILPGEIFKYKWTVTVEDGPTKSDPRCLTRYY
SSFVNMERDLASGLIGPLLICYKESVDQRGNQIMSDKRNVILFSVFDEN
RSWYLTENIQRFLPNPAGVQLEDPEFQASNIMHSINGYVFDSLQLSVCL
HEVAYWYILSIGAQTDFLSVFFSGYTFKHKMVYEDTLTLFPFSGETVFM
SMENPGLWILGCHNSDFRNRGMTALLKVSSCDKNTGDYYEDSYEDISAY
LLSKNNAIEPRSFSQNSRHPSTRQKQFNATTIPENDIEKTDPWFAHRTP
MPKIQNVSSSDLLMLLRQSPTPHGLSLSDLQEAKYETFSDDPSPGAIDS
NNSLSEMTHFRPQLHHSGDMVFTPESGLQLRLNEKLGTTAATELKKLDF
KVSSTSNNLISTIPSDNLAAGTDNTSSLGPPSMPVHYDSQLDTTLFGKK
SSPLTESGGPLSLSEENNDSKLLESGLMNSQESSWGKNVSSTESGRLFK
GKRAHGPALLTKDNALFKVSISLLKTNKTSNNSATNRKTHIDGPSLLIE
NSPSVWQNILESDTEFKKVTPLIHDRMLMDKNATALRLNHMSNKTTSSK
NMEMVQQKKEGPIPPDAQNPDMSFFKMLFLPESARWIQRTHGKNSLNSG
QGPSPKQLVSLGPEKSVEGQNFLSEKNKVVVGKGEFTKDVGLKEMVFPS
SRNLFLTNLDNLHENNTHNQEKKIQEEIEKKETLIQENVVLPQIHTVTG
TKNFMKNLFLLSTRQNVEGSYDGAYAPVLQDFRSLNDSTNRTKKHTAHF
SKKGEEENLEGLGNQTKQIVEKYACTTRISPNTSQQNFVTQRSKRALKQ
FRLPLEETELEKRIIVDDTSTQWSKNMKHLTPSTLTQIDYNEKEKGAIT
QSPLSDCLTRSHSIPQANRSPLPIAKVSSFPSIRPIYLTRVLFQDNSSH
LPAASYRKKDSGVQESSHFLQGAKKNNLSLAILTLEMTGDQREVGSLGT
SATNSVTYKKVENTVLPKPDLPKTSGKVELLPKVHIYQKDLFPTETSNG
SPGHLDLVEGSLLQGTEGAIKWNEANRPGKVPFLRVATESSAKTPSKLL
DPLAWDNHYGTQIPKEEWKSQEKSPEKTAFKKKDTILSLNACESNHAIA
AINEGQNKPE1EVTWAKQGRTERLCSQNPPVLKRHQREITRTTLQSDQE
EIDYDDTISVEMKKEDFDIYDEDENQSPRSFQKKTRHYFIAAVERLWDY
GMSSSPHVLRNRAQSGSVPQFKKVVFQEFTDGSFTQPLYRGELNEHLGL
LGPYIRAEVEDNIMVTFRNQASRPYSFYSSLISYEEDQRQGAEPRKNFV
KPNETKTYFWKVQHHMAPTKDEFDCKAWAYFSDVDLEKDVHSGLIGPLL
VCHTNTLNPAHGRQVTVQEFALFFTIFDETKSWYFTENMERNCRAPCNI
QMEDPTFKENYRFHAINGYIMDTLPGLVMAQDQRIRWYLLSMGSNENIH
SIHFSGHVFTVRKKEEYKMALYNLYPGVFETVEMLPSKAGIWRVECLIG
EHLHAGMSTLFLVYSNKCQTPLGMASGHIRDFQITASGQYGQWAPKLAR
LHYSGSINAWSTKEPFSWIKVDLLAPMIIHGIKTQGARQKFSSLYISQF
IIMYSLDGKKWQTYRGNSTGTLMVFFGNVDSSGIKHNIFNPPIIARYIR
LHPTHYSIRSTLRMELMGCDLNSCSMPLGMESKAISDAQITASSYFTNM
FATWSPSKARLHLQGRSNAWRPQVNNPKEWLQVDFQKTMKVTGVTTQGV
KSLLTSMYVKEFLISSSQDGHQWTLFFQNGKVKVFQGNQDSFTPVVNSL
DPPLLTRYLRIHPQSWVHQIALRMEVLGCEAQDLY The factor VIII molecules according to the present invention may be B domain truncated Factor FVIII molecules wherein the remaining domains correspond closely to the sequence as set forth in amino acid no 1-740 and 1649-2332 in SEQ ID NO. 2 although there may also be one or more alterations within the vWF binding region between residues 1670-1684. A preferred B domain linker (21 amino acids) according to the present invention is set forth in SEQ ID NO 4 (SFSQNSRHPSQNPPVLKRHQR). FVIII molecules according to the invention may differ slightly from the sequence set forth in SEQ ID NO 2, meaning that the remaining domains (i.e. the three A-domains and the two C-domains) may differ slightly e.g. 1, 2, 3, 4, 5, 6, 7, 8, 9, or 10 amino acids or more, such as about 1%, 2%, or 3% from the amino acid sequence as set forth in SEQ ID NO 2 (amino acids 1-740 and 1649-2332) due to the fact that mutations can be introduced in order to e.g. reduce vWF binding capacity. Furthermore, it is plausible that amino acid modifications (substitutions, deletions, etc.) are introduced other places in the molecule in order to modify the binding capacity of Factor VIII with various other components such as e.g. LRP, various receptors, other coagulation factors, cell surfaces, introduction and/or abolishment of glycosylation sites, etc.

Factor VIII molecules according to the present invention have Factor VIII activity, meaning the ability to function in the coagulation cascade in a manner functionally similar or equivalent to FVIII, induce the formation of FXa via interaction with FIXa on an activated platelet, and support the formation of a blood clot. The activity can be assessed in vitro by techniques well known in the art such as e.g. clot analysis, endogenous thrombin potential analysis, etc. Factor VIII molecules according to the present invention have FVIII activity being at least about 10%, at least 20%, at least 30%, at least 40%, at least 50%, at least 60%, at least 70%, at least 80%, at least 90%, and 100% or even more than 100% of that of native human FVIII.

Endogenous full length FVIII is synthesized as a single-chain precursor molecule. Prior to secretion, the precursor is cleaved into the heavy chain and the light chain. Recombinant B domain-deleted FVIII can be produced from two different strategies. Either the heavy chain without the B-domain and the light chain are synthesized individually as two different polypeptide chains (two-chain strategy) or the B-domain deleted FVIII is synthesized as a single precursor polypeptide chain (single-chain strategy) that is cleaved into the heavy and light chains in the same way as the full-length FVIII precursor.

In a B domain-deleted FVIII precursor polypeptide, the heavy and light chain moieties are normally separated by a linker. To minimize the risk of introducing immunogenic epitopes in the B domain-deleted FVIII, the sequence of the linker is preferable derived from the FVIII B-domain. As a minimum, the linker must comprise a recognition site for the protease that cleaves the B domain-deleted FVIII precursor polypeptide into the heavy and light chain. In the B domain of full length FVIII, amino acid 1644-1648 constitutes this recognition site. The thrombin site leading to removal of the linker on activation of B domain-deleted FVIII is located in the heavy chain. Thus, the size and amino acid sequence of the linker is unlikely to influence its removal from the remaining FVIII molecule by thrombin activation. Deletion of the B domain is an advantage for production of FVIII. Nevertheless, parts of the B domain can be included in the linker without reducing the productivity. The negative effect of the B domain on productivity has not been attributed to any specific size or sequence of the B domain.

The truncated B-domain may contain several O-glycosylation sites. However, according to a preferred embodiment, the molecule comprises only one, alternatively two, three or four O-linked oligosaccharides in the truncated B-domain. According to a preferred embodiment, the truncated B domain comprises only one potential O-glycosylation sites and one or more hydrophobic moieties are covalently conjugated to this O-glycosylation site, preferably via a linker. The Factor VIII molecule also contains a number of N-linked oligosaccharides and each of these may potentially serve as an anchor for attachment of a hydrophobic side group.

The length of the B domain in the wt FVIII molecule is about 907 amino acids. The length of the truncated B domain in molecules according to the present invention may vary from about 10 to about 800 amino acids, such as e.g. from about 10 amino acids to about 700 acids, such as e.g. about 12-500 amino acids, 12-400 amino acids, 12-300 amino acids, 12-200 amino acids, 15-100 amino acids, 15-75 amino acids, 15-50 amino acids, 15-45 amino acids, 20-45 amino acids, 20-40 amino acids, or 20-30 amino acids. The truncated B-domain may comprise fragments of the heavy chain and/or the light chain and/or an artificially introduced sequence that is not found in the wt FVIII molecule. The terms "B-domain truncated" and "B-domain deleted" may be used interchangeably herein.

Von Willebrandt Factor (vWF): vWF is a large mono-/multimeric glycoprotein present in blood plasma and produced constitutively in endothelium (in the Weibel-Palade bodies), megakaryocytes (α-granules of platelets), and subendothelial connective tissue. Its primary function is binding to other proteins, particularly Factor VIII and it is important in platelet adhesion to wound sites. Factor VIII is bound to vWF while inactive in circulation; Factor VIII degrades rapidly or is cleared when not bound to vWF. It thus follows that reduction or abolishment of vWF binding capacity in FVIII has thus far been considered as a highly undesirable approach in obtaining Factor FVIII variants with prolonged circulatory half life.

The term "reduced capacity to bind vWF" is herein meant to encompass Factor VIII variants, wherein the capacity to bind vWF is decreased by at least 50%, preferably by at least 60%, more preferably by at least 70%, more preferably by at least 80%, more preferably by at least 90%, and most preferably about 100%. FVIII binding to vWF may be measured either by an ELISA like assay or as direct binding to immobilized vWF using surface plasmon resonance. The region in Factor VIII responsible for binding to vWF is the region spanning residues 1670-1684 as disclosed in EP0319315. It is envisaged that Factor VIII point and/or deletion mutants involving this area will modify the ability to bind to vWF. Examples of particularly preferred point mutations according to the present invention include variants comprising one or more of the following point mutations: Y1680F, Y1680R, Y1680N, and E1682T, and Y1680C. Without being bound by theory it is envisaged that the reason why it may be advantageous to attach hydrophobic side groups to Factor VIII molecules with reduced vWF binding capacity rather than attaching such side groups to Factor VIII molecules with normal vWF binding capacity, is that the size of the side group is relatively small in the large Factor VIII/vWF complex. It is hypothesized that a relatively large side group functions more efficiently in shielding the free Factor VIII from clearance.

Factor IX: Factor IXa (FIXa) is a trypsin-like serine protease that serves a key role in haemostasis by generating, as part of the tenase complex, most of the factor Xa required to support proper thrombin formation during coagulation (reviewed in (Hoffman and Monroe, III 2001)). Factor IX (FIX) is a vitamin K-dependent coagulation factor with structural similarities to factor VII, prothrombin, factor X, and protein C. The circulating zymogen form consists of 415 amino acids divided into four distinct domains comprising an N-terminal γ-carboxyglutamic acid-rich (Gla) domain, two EGF domains and a C-terminal trypsin-like serine protease domain. Activation of FIX occurs by limited proteolysis at Arg145-Ala146 and Arg180-Val181 releasing a 35-aa fragment, the so-called activation peptide (Schmidt and Bajaj 2003). The activation peptide is heavily glycosylated, containing two N-linked and up to four O-linked glycans.

"Factor IX" or "FIX", as used herein, refers to a human Factor IX glycoprotein that is a member of the intrinsic coagulation pathway and is essential to blood coagulation. "Factor IX(a)" includes natural allelic variants of FIX(a) that may exist and occur from one individual to another. Factor IX(a) may be plasma-derived or recombinantly produced using well known methods of production and purification. The degree and location of glycosylation, gamma-carboxylation and other post-translation modifications may vary depending on the chosen host cell and its growth conditions. Unless otherwise specified or indicated, Factor IX means any functional human Factor IX protein molecule in its normal role in coagulation, including any fragment, analogue and derivative thereof. One example of a "wild type FIX" is the full length human FIX molecule, as shown in SEQ ID NO:3.

The terms "analogue" or "analogues", or "variants" as used herein, is intended to designate Factor FIX having the sequence of SEQ ID NO:3, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both. The "analogue" or "analogues" within this definition still have FIX activity in its activated form. In one embodiment a variant is at least 90% identical with the sequence of SEQ ID NO: 3. In a further embodiment a variant is at least 95% identical with the sequence of SEQ ID NO: 3. As used herein any reference to a specific positions refers to the corresponding position in SEQ ID NO: 3.

Unless otherwise specified, factor IX domains include the following amino acid residues: Gla domain being the region from reside Tyr1 to residue Lys43; EGF1 being the region from residue Gln44 to residue Leu84; EGF2 being the region from residue Asp85 to residue Arg145; the Activation Peptide being the region from residue Ala146 to residue Arg180; and the Protease Domain being the region from residue Val181 to Thr414. The light chain refers to the region encompassing the Gla domain, EGF1 and EGF2, while the heavy chain refers to the Protease Domain.

```
SEQ ID NO. 3:
Wild type human coagulation Factor IX
YNSGKLyyFVQGNLyRyCMyyKCSFyyARyVFyNTyRTTyFWKQYVDGD

QCESNPCLNGGSCKDDINSYECWCPFGFEGKNCELDVTCNIKNGRCEQF

CKNSADNKVVCSCTEGYRLAENQKSCEPAVPFPCGRVSVSQTSKLTRAE

AVFPDVDYVNSTEAETILDNITQSTQSFNDFTRVVGGEDAKPGQFPWQV

VLNGKVDAFCGGSIVNEKWIVTAAHCVETGVKITVVAGEHNIEETEHTE

QKRNVIRIIPHHNYNAAINKYNHDIALLELDEPLVLNSYVTPICIADKE

YTNIFLKFGSGYVSGWGRVFHKGRSALVLQYLRVPLVDRATCLRSTKFT

IYNNMFCAGFHEGGRDSCQGDSGGPHVTEVEGTSFLTGIISWGEECAMK

GKYGIYTKVSRYVNWIKEKTKLT
```

γ: Represents gamma-carboxylated Glu ('E') remains. In fully gamma-carboxylated FIX, the first 12 Glu residues are gamma-carboxylated, but there are variants (especially in the case of recombinant FIX products) in which less gamma-carboxylation is observed.

Note that a dimorphism is present in FIX at position 148, which can be either Ala or Thr (see McGraw et al. (1985) *PNAS*, 82:2847). Ala is present in N9-GP (rFIX glycopegylated) and BeneFIX, whereas FIX:Fc produced by Biogen Idec carries a Thr. FIX molecules according to the present invention can thus have either an Ala or a Thr residue in position 148.

Activity determination of FIX conjugates can be carded out using the methods described in the art, such as a one stage activated partial thromboplastin time assay as described in, for example, Biggs (1972, Human Blood Coagulation Haemostasis and Thrombosis (Ed. 1), Oxford, Blackwell, Scientific, pg. 614). Briefly, to assay the biological activity of a Factor IX molecule as described herein, the assay can be performed with equal volumes of activated partial thromboplastin reagent, Factor IX deficient plasma isolated from a patient with hemophilia B using sterile phlebotomy techniques well known in the art or Factor IX immunodepleted plasma (commercial available from e.g. Helena Laboratories or ILS), normal pooled plasma as standard, or the sample, and 25 mM calcium. In this assay, one unit of activity is defined as that amount present in one of normal pooled plasma. Alternatively, the activity can be measured against a normal human plasma pool which has been calibrated against a WHO human FIX standard (NIBSC). Further, art assay for biological activity based on the ability of Factor IX to reduce the clotting time of plasma from Factor IX-deficient patients to normal can be performed as described in, for example, Proctor and Rapaport (Amer. J. Olin. Path. 36: 212 (1961)).

Fusion protein: Fusion proteins/chimeric proteins, are proteins created through the joining of two or more genes which originally coded for separate proteins. Translation of this fusion gene results in a single polypeptide with functional properties derived from each of the original proteins. Therapeutic proteins such as e.g. coagulation factor molecules according to the present invention may be fused to another polypeptide, e.g. an antibody binding polypeptide such as e.g. an Fc receptor. The proteins according to the invention may also be fused to Fc domains, preferably Fc domains comprising mutations resulting in reduced effector functions and/or mutations resulting in increased affinity to the neonatal Fc receptor. Compared to coagulation factors, such as e.g. Factor VIII, antibodies have a very long half life. It may thus be possible to prolong the half life of coagulation factors such as e.g. Factor VII, Factor VIII, and Factor IX significantly by non covalent complex formation between a coagulation Factor Fc receptor fusion protein and a circulating antibody.

Modified circulatory half life: Proteins according to the present invention have a modified circulatory half life compared to the wild type protein molecule, preferably an increased circulatory half life. Circulatory half life is preferably increased at least 10%, preferably at least 15%, preferably at least 20%, preferably at least 25%, preferably at least 30%, preferably at least 35%, preferably at least 40%, preferably at least 45%, preferably at least 50%, preferably at least 55%, preferably at least 60%, preferably at least 65%, preferably at least 70%, preferably at least 75%, preferably at least 80%, preferably at least 85%, preferably at least 90%, preferably at least 95%, preferably at least 100%, more preferably at least 125%, more preferably at least 150%, more preferably at least 175%, more preferably at least 200%, and most preferably at least 250% or 300%. Even more preferably, such molecules have a circulatory half life that is increased at least 400%, 500%, 600%, or even 700%.

Hydrophobic side chain/hydrophobic side group: The proteins according to the present invention are conjugated with a side group. In this connection, a "side group" is to be understood as a side group that is largely hydrophobic in nature, and wherein said side group is not naturally a part of the protein molecule.

When conjugated to a protein, such hydrophobic side groups may extend the in vivo circulation half-life of the protein compared to the un-conjugated protein. These hydrophobic side groups may herein be referred to as "albumin binders" and include derivatives of fatty acids. These groups may or may not have affinity for albumin, in vitro or in vivo. The attachment of albumin-binders to proteins or peptides has been shown to potentially increase the plasma half life of said proteins or peptides. A class of typical albumin binders are derived from fatty acids, because albumin is capable to bind highly hydrophobic molecules. Therefore, compounds having a —$(CH_2)_{12}$— moiety are possible albumin binders in the context of this invention. If such a compound is attached to a protein or peptide and results in an increased plasma half life of said protein or peptide, it is understood that the albumin binder may contribute to the overall increase of plasma half life by either binding to albumin and/or by other mechanisms. In one embodiment, the albumin binder-protein conjugate is a molecule in which a single albumin binder has been attached to the protein. In other embodiments, more than one albumin binder has been attached to the protein, such as two, three, four, five, or more.

The albumin binding moiety may comprise a portion which is particularly relevant for the albumin binding and thereby the extended circulation in the blood stream, which portion may accordingly be referred to as a half life extending moiety. The half life extending moiety is preferably at, or near, the opposite end of the moiety used as attachment point to the peptide. The remaining part of the albumin binding moiety, i.e. the part in-between the half life extending moiety and the moiety used as point of attachment to the peptide, may be referred to as a linker moiety, linker, spacer, or the like. However, the presence of a linker is optional, and hence the albumin binding moiety may be identical to the half life extending moiety.

In particular embodiments, the albumin binding moiety and/or the half life extending moiety is lipophilic, and/or negatively charged at physiological pH (7.4). In a preferred embodiment, the albumin binding moiety and/or the half life extending moiety is covalently linked, optionally through a linker, to an amino group of a sialic acid residue or a sialic acid derivative, via an amide bond. According to a highly preferred embodiment of the present invention, the albumin binding moiety is attached to a glycol-protein using enzymatic methods such as e.g. a method involving use of a sialyltransferase.

For the present purposes, the terms "albumin binding moiety", "half life extending moiety", and "linker" include the un-reacted as well as the reacted forms of these molecules. Whether or not one or the other form is meant is clear from the context in which the term is used. The term "fatty acid" refers to aliphatic monocarboxylic acids having from 4 to 28 carbon atoms, it is preferably unbranched, and/or even numbered, and it may be saturated or unsaturated. The term "fatty diacid" refers to fatty acids as defined above but with an additional carboxylic acid group in the omega position. Thus, fatty diacids are dicarboxylic acids. The nomenclature is as is usual in the art, for example —COOH, as well as HOOC—, refers to carboxy; —$C_6H_4$— to phenylen; —CO—, as well as —OC—, to carbonyl (O=C<); and $C_6H_5$—O— to phenoxy.

In a preferred embodiment, the albumin binding moiety of the present invention comprises a fatty acyl group (—$(CH_2)_n$—CO—, where n=1, 2, 3, . . . 40) or an omega-carboxy fatty acyl group ($HO_2C$—$(CH_2)_n$—CO—, where n=1, 2, 3, . . . 40) linked to the peptide or protein via a linker and a sialic acid residue or sialic acid derivative.

In a preferred embodiment the linker moiety, if present, has from 2 to 80 C-atoms, preferably from 5 to 70 C-atoms. In additional preferred embodiments, the linker moiety, if present, has from 4 to 60 hetero atoms, preferably from 2 to 40 hetero atoms, more preferably from 3 to 30 hetero atoms. Particularly preferred examples of hetero atoms are N-, O-, and S-atoms. H and C-atoms are not hetero atoms.

In another embodiment, the linker comprises at least one OEG molecule, and/or at least one glutamic acid residue, or rather the corresponding radicals (OEG designates 8-amino-3,6-dioxaoctanic acid, i.e. this radical: —NH—$(CH_2)_2$—O—$(CH_2)_2$—O—$CH_2$—CO—).

In one preferred embodiment, the linker moiety comprises a di-carboxamide moiety linked to a sialic acid residue by an amide bond. In preferred examples, the di-carboxamide residue has from 2-30 C-atoms, preferably 4-20 C-atoms, more preferably 4-10 C-atoms. In additional preferred examples, the di-carboxamide residue has from 0-10 hetero-atoms, preferably 0-5 hetero-atoms.

In another preferred example, the linker moiety comprises a group containing both an amino group and a distal carboxyl-group linked to a sialic acid residue by an amide bond through its distal carboxyl groups. In one preferred embodiment this group is an OEG group.

The amino acid glutamic acid (Glu) comprises two carboxylic acid groups. Its gamma-carboxy group is preferably used for forming an amide bond with an amino group of a sialic acid residue or a sialic acid derivative, or with an amino group of an OEG molecule, if present, or with the amino group of another Glu residue, if present. The amino group of Glu in turn forms an amide bond with the carboxy group of the half life extending moiety, or with the carboxy group of an OEG molecule, if present, or with the gamma-carboxy group of another Glu, if present. This way of inclusion of Glu is occasionally briefly referred to as "gamma-Glu".

An individual protein according to the invention may thus comprise side groups of both hydrophilic and hydrophobic nature. It furthermore follows that it is possible to conjugate proteins according to the invention with hydrophobic side groups as well as one or more side groups that are not necessarily hydrophobic in nature; e.g. hydrophiliers, polypeptides, etc.

In a broad aspect the present invention relates to a stable conjugate to proteins which comprises a) one or more N-linked glycans, and/or b) one or more O-linked glycans, wherein hydrophobic side groups (albumin binding residues) are linked to said one or more glycans in said protein, optionally via a hydrophilic spacer, or a pharmaceutically acceptable salt, solvate or prodrug thereof. The glycans may be naturally occurring or they may be genetically engineered into the proteins according to the invention In one embodiment the side chain is linked to the protein via one or more of its N-linked glycans. In another embodiment the side chain is linked to the protein via one or more of its O-linked glycans. In a further embodiment the side chain is linked to the protein via both its N-linked glycans and its O-linked glycans. In a preferred embodiment the protein is a coagulation factor.

In one embodiment of the present invention the hydrophilic spacer has a Log P<0.

Solubility of a hydrophilic spacer can be described by its log P value. Log P, also known as the partition coefficient, is the logarithm of the ratio of concentrations of a compound in the two phases of a mixture of two immiscible solvents at equilibrium. Typically one of the solvents is water while the second is selected from octan-1-ol, chloroform, cyclohexane and propylene glycol dipelargonate (PGDP). Log P values measured in these different solvents show differences principally due to hydrogen bonding effects. Octanol can donate and accept hydrogen bonds whereas cyclohexane is inert. Chloroform can donate hydrogen bonds whereas PGDP can only accept them.

In another embodiment of the invention, the hydrophilic spacer has a Log P of below −0.5 in either octan-1-ol, chloroform, cyclohexane and propylene glycol dipelargonate (PGDP). In a further embodiment, the hydrophilic spacer has a log P below −1 in either octan1-ol, chloroform, cyclohexane and propylene glycol dipelargonate (PGDP).

Alternatively, the Log P value can be calculated as m Log P and/or c Log P for the albumin binder part or hydrophilic spacer part using published algorithms (T. Fujita; J. Iwasa and C. Hansch, *J. Am. Chem. Soc.* 86, 5175-5180, (1964) "A New Substituent Constant, Pi, Derived from Partition Coefficients", C. A. Lipinski et al. *Advanced Drug Delivery Reviews,* 23, 3-25, (1997) "Experimental and Computational Approaches to Estimate Solubility and Permeability in Drug Discovery and Development Settings" and I. Moriguchi, S. Hirono, I. Nakagome, H. Hirano, *Chem. Pharm. Bull.* 42, 976-978, (1994) "Comparison of Reliability of log P Values for Drugs Calculated by Several Methods"). In a further embodiment the protein is linked to one albumin binding residue via a linker.

In another embodiment each type of glycan of the protein is linked to one or two or more albumin binding residues via one or two or more linkers. These albumin binding residues may be identical or non-identical. Also, these linkers may be identical or non-identical. Thus, in one example one or two or more albumin binding residues are linked via one linker to one type of glycan of the protein and, in addition, one or two or more albumin binding residues are linked via a linker to another type of glycan of the protein. Alternatively the albumin binding residues are linked via one or more types of glycans in addition to other sites on the protein, such as e.g. a native or a recombinantly introduced cysteine residue, one or both N-terminals, one or both C-terminals, a glutamine residue, or a lysine residue. Preferred examples of such glycans are bifurcated complex N-glycans and core-1 type O-glycans.

In another embodiment, the protein has been recombinantly engineered to contain more glycans than the native protein. These glycans are amenable to modification with the albumin binding residues of the invention.

In a further embodiment the protein has one or more modifications in addition to the hydrophobic side chains. Thus, the protein may be linked to one or more hydrophilic polymers such as but not limited to eg. PEG, polysialic acid, hydroalkyl starch, dextran, dendrimers, etc. In one embodiment, the hydrophilic polymer is linked to one of the glycans of the protein, while the hydrophobic side chain is linked to another of the glycans of the protein. In a particular embodiment, the hydrophilic polymer is a PEG linked to the O-glycans of a FVIII molecule, while the hydrophobic side chain is linked the N-glycans of said FVIII molecule. In another particular embodiment, the hydrophilic polymer is a PEG linked to the N-glycans of the FVIII molecule, while the hydrophobic side chain is linked the O-glycans of the FVIII molecule.

In a further aspect the present invention relates to a protein conjugate wherein the conjugate has the formula (I):

Wherein
asialoProtein represents a protein in which the terminal sialic acid has been removed from a glycan and z is an integer of the value 1, 2, 3, 4, 5, 6, 7, 8, 9, or 10.
B2 represents a glycyl-sialic acid with the structure

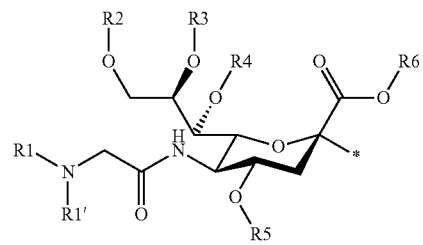

wherein R1, R1', R2, R3, R4, R5, and R6 are either a bond connecting B2 with B1 or a hydrogen and wherein * denotes the connection to asialoCoagulationFactor. Thus a bond ending in a * represents only a bond, i.e. an open bond.
B1 represents a linker
W is a chemical group linking A and B1, and
A represents a hydrophobic albumin binding side group; and pharmaceutically acceptable salts, solvates and prodrugs thereof.

In a preferred embodiment, A comprises a hydrophobic group such as an alkylene chain *—(CH$_2$)$_n$—* were n=8-26 optionally connected to aryl substituents, and a negatively charged group such as carboxylic, sulfonic, sulfenic, sulfinic, phosphonic or phosphinic acid, acylsulfonamide, carboxylic acid isosteres such as tetrazole, hydroxy oxazole or the like.

In a further embodiment A has the structure

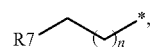

wherein * denotes the attachment to B1 through W, thus a bond ending in a * represents only a bond, i.e. an open bond. R7 is hydrogen, —COOH, tetrazolyl, or —C(=O)—NHS (=O)2-R7a,

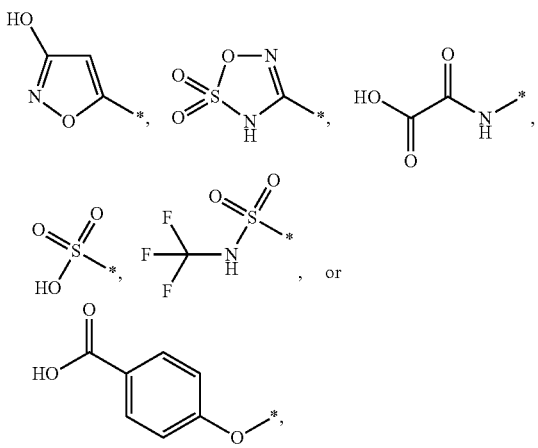

n is selected from 7, 8, 9, 10, 11, 12, 13, 14, 15, 16, 17, 18, 19, 20, 21, 22, 23, 24, and 25, and R7a is selected from $C_{1-6}$alkyl, phenyl, or $C_{1-6}$alkylphenyl, wherein * denotes the attachment to the remaining part of group A. In a further embodiment R7 is —COOH. In another embodiment n is selected from 14, 16, and 18. In a further embodiment R7 is —COOH and n is selected from 14, 16, and 18.

In a further embodiment A is selected from the following list

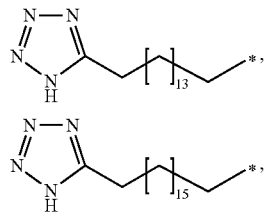

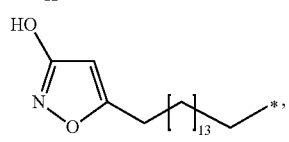

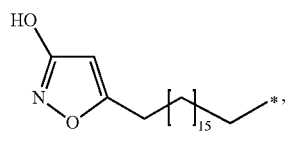

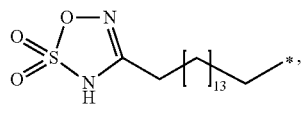

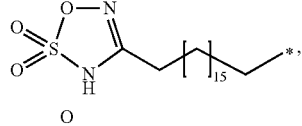

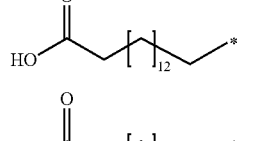

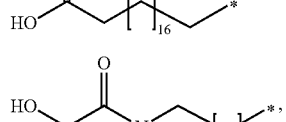

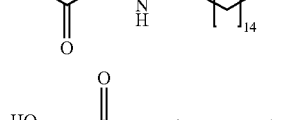

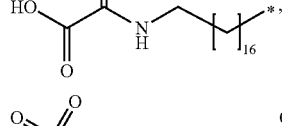

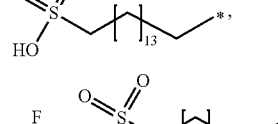

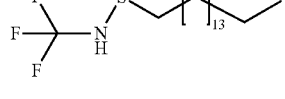

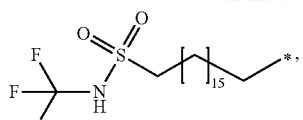

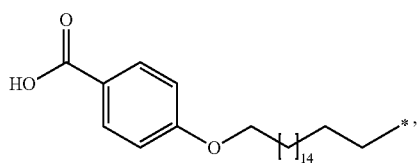

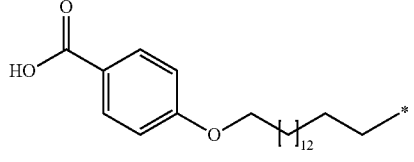

as well as $CH_3—(CH_2)_n—*$ groups were n=8-26 wherein * denotes the attachment to B1 through W, thus a bond ending in a * represents only a bond, i.e. an open bond.

In a further embodiment W is —CONH—

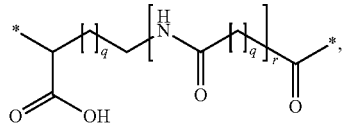

where q=0-10 and r=0 or 1

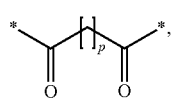

where p=1-20

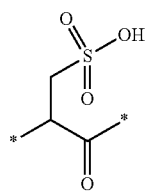 [SMILES: *C(=O)C(*)CS(=O)(=O)O]

C3-C10 cycloalkyl

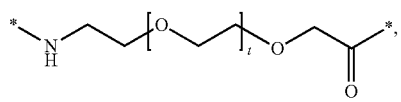

where t=0-10

*—$SO_2$—$(CH_2)_n$* interlinking structural elements of B1 optionally via a nitrogen atom or linked to an amine of B2.

In a further embodiment B1 is selected from the following list
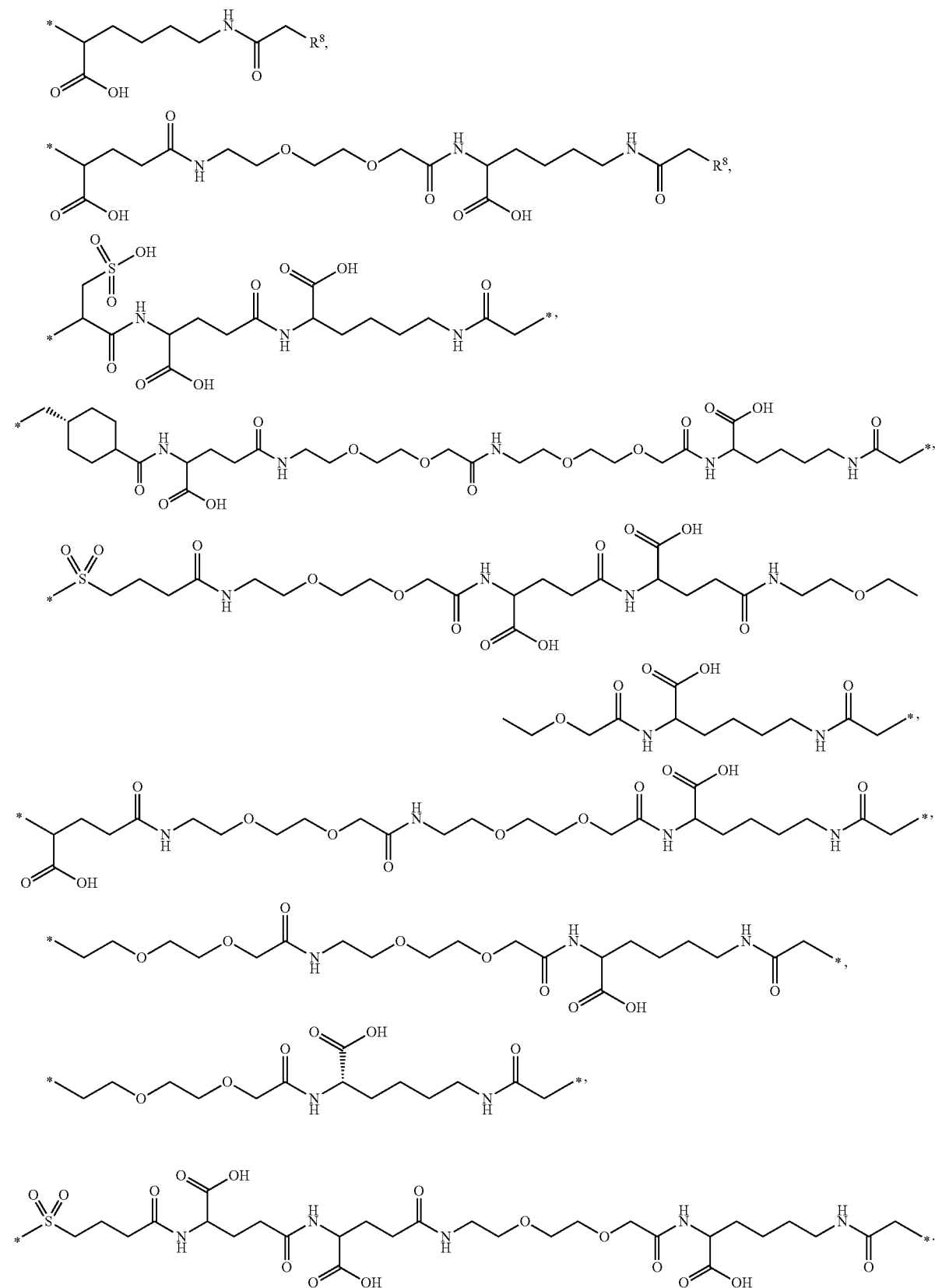

-continued
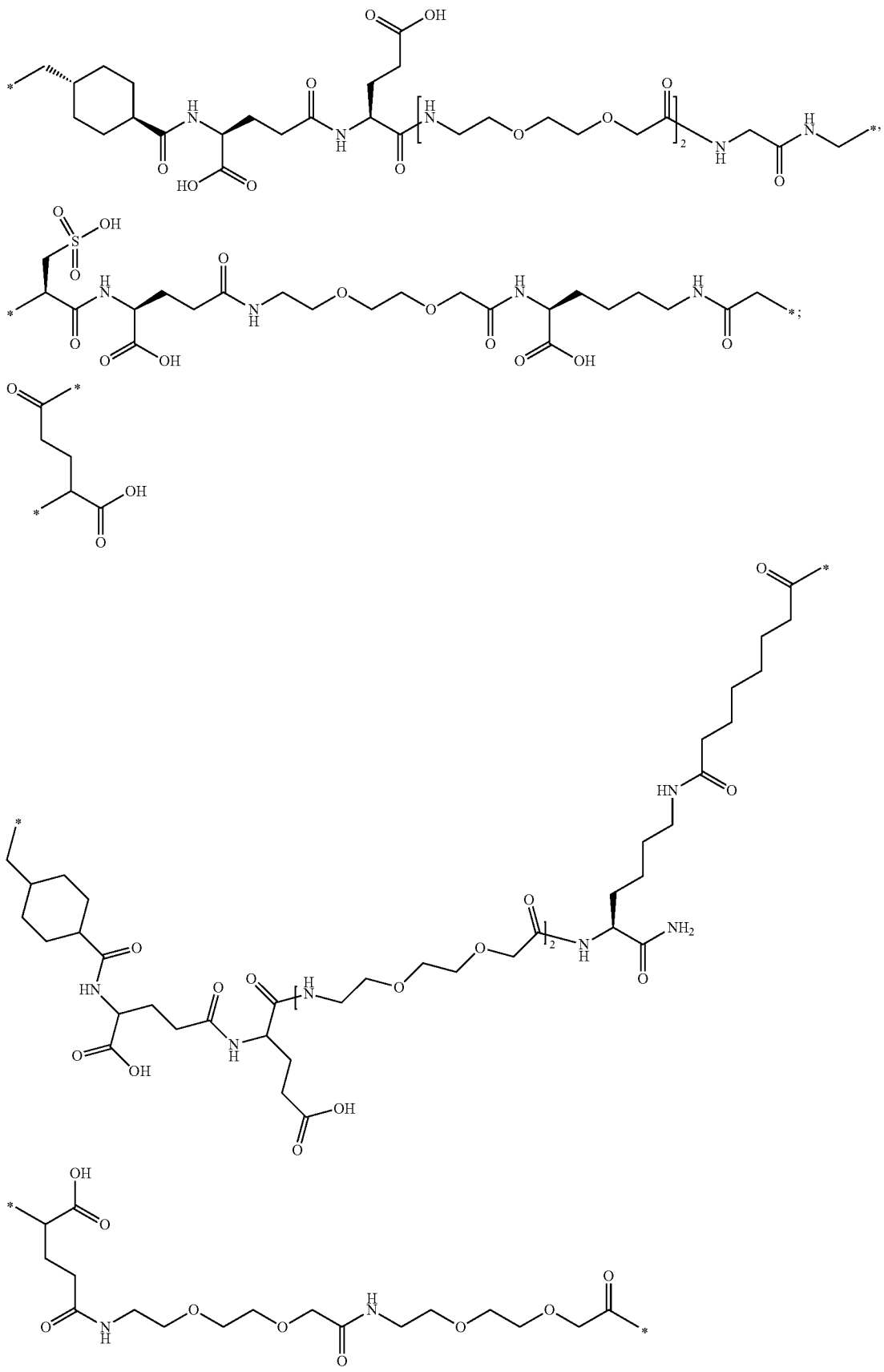

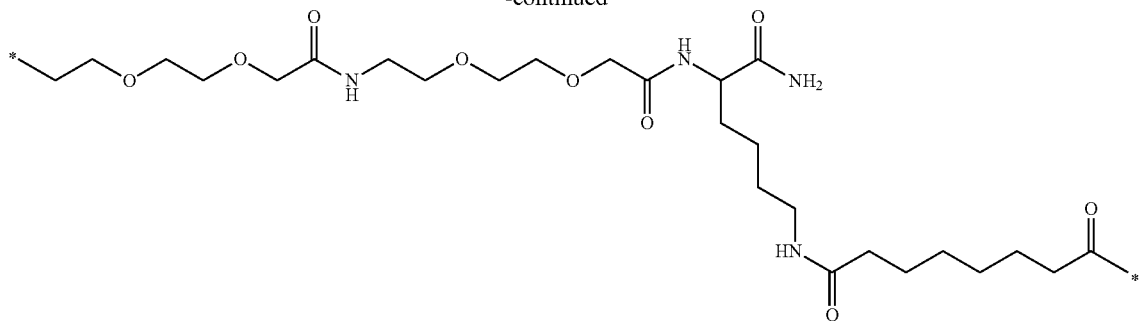
15
wherein * denote the attachment to B2 and W
In a particular embodiment, R1, R1', R3, R4, R5, and R6 are a hydrogen and R2 is connected to B1. In a further particular embodiment R1', R2, R3, R4, R5, and R6 are a hydrogen and R1 is connected to B1.
In a further embodiment the protein conjugate is selected from the following list
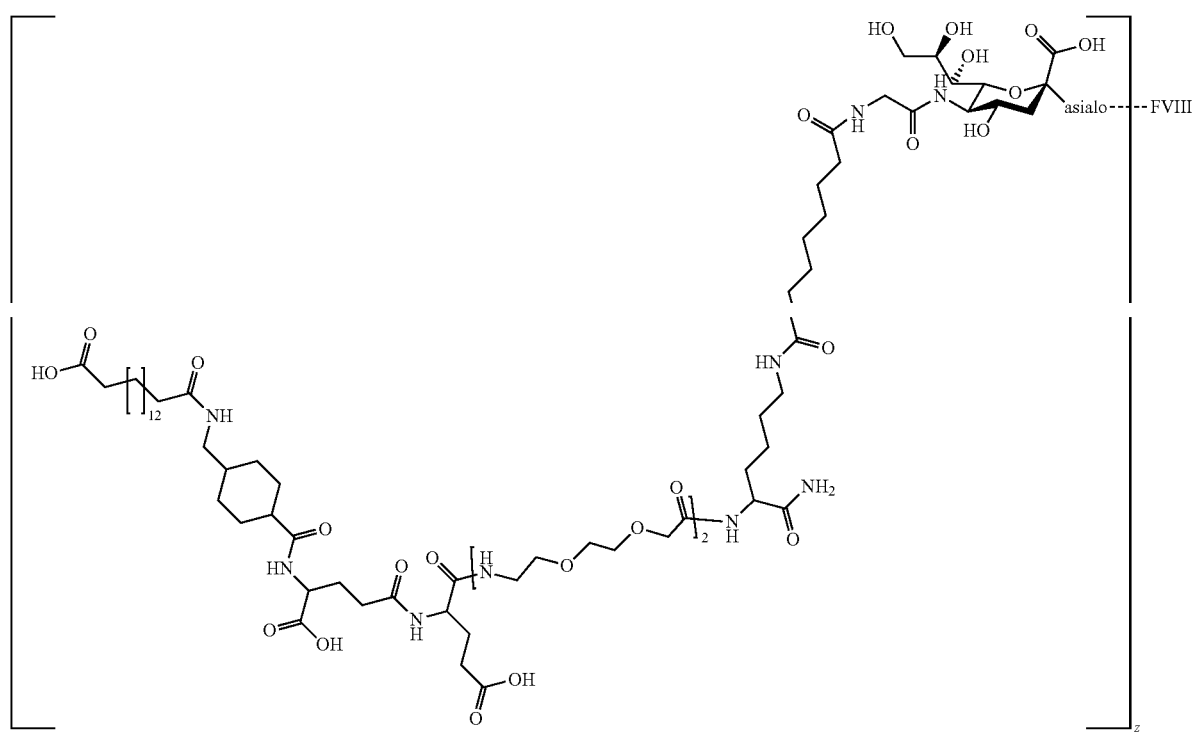
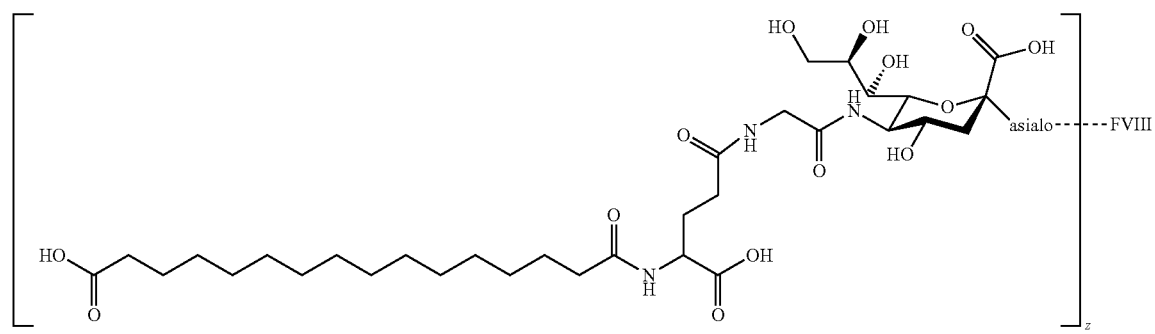

-continued
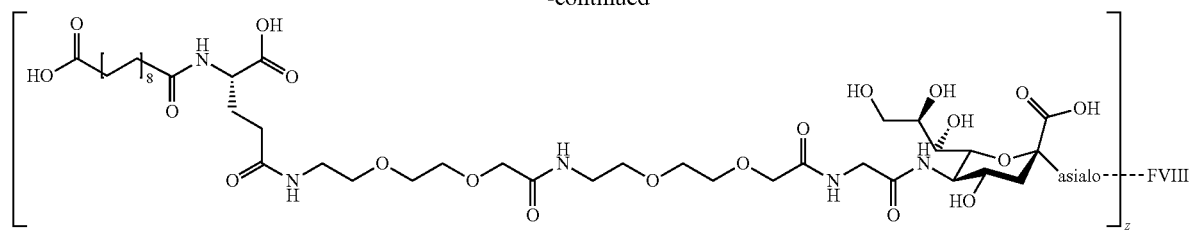
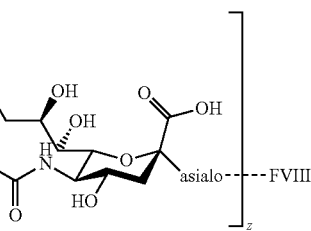
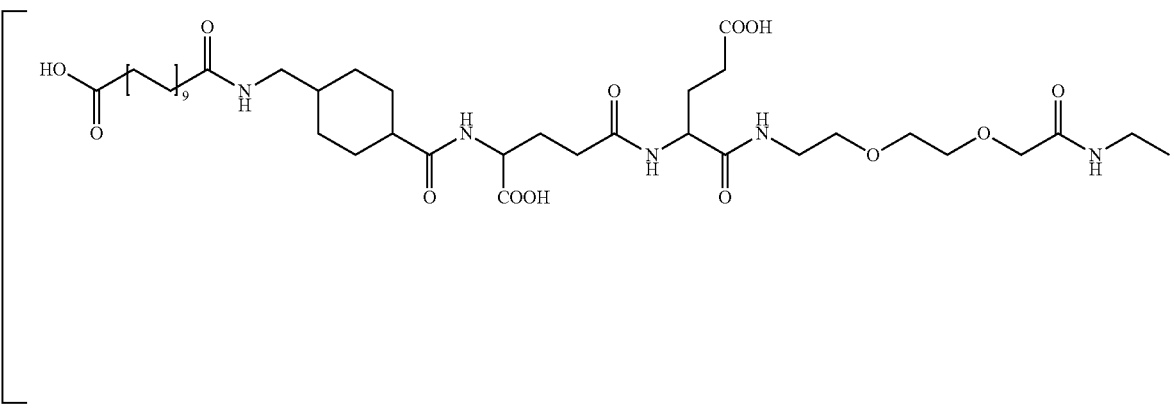
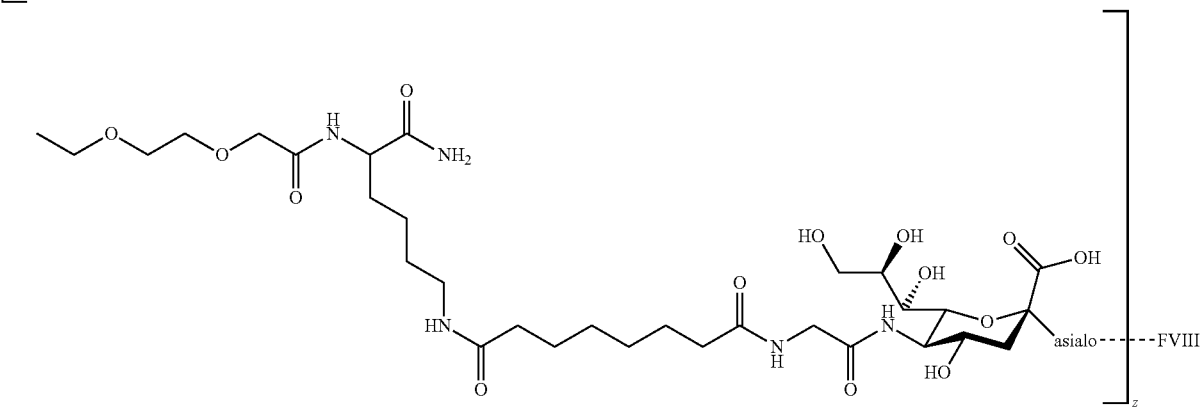
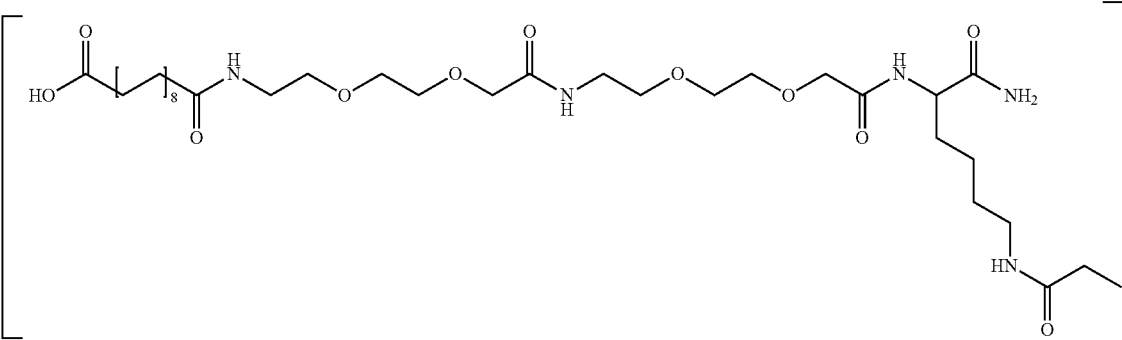
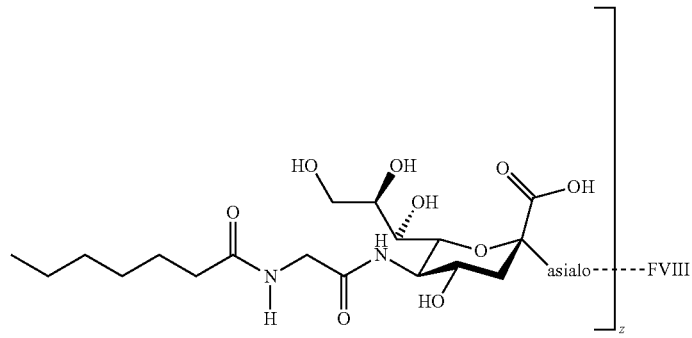

wherein one, two, three, four or five side chains are attached per protein molecule (z=1, 2, 3, 4, or 5). In a particular embodiment, one, two, three or four side chains are attached to the N-glycans of the protein. In another particular embodiment, a side chain is attached to an O-glycan. In another particular embodiment, one, two, three or four side chains are attached to FVIII N-glycans in addition to a side chain being attached to a FVIII O-glycan. In a further particular embodiment, one, two, three or four side chains are attached to the FVIII N-glycans in addition to a 40 kDa PEG being attached to the FVIII O-glycan. In a further embodiment, one, two, three or four side chains are attached to the one or two of the FVIIa N-glycans while another glycan is modified with PEG. In another embodiment, one, two, three or four side chains are attached to the one or two of the FIX N-glycans while another, or the same (branched) glycan is modified with PEG.

Glycoprotein: The term "glycoprotein" is intended to encompass peptides, oligopeptides and polypeptides containing one or more oligosaccharides (glycans) attached to one or more amino acid residues of the "back bone" amino acid sequence. The glycans may be N-linked or O-linked. The glycans may be naturally occurring and/or inserted into the protein by genetic engineering.

N- and O-linked oliqosaccharide: As used herein, the term "glycan" or, interchangeable, "oligosaccharide chain" refers to the entire oligosaccharide structure that is covalently linked to a single amino acid residue. Glycans are normally N-linked or O-linked, e.g., glycans are linked to an asparagine residue (N-linked glycosylation) or a serine or threonine residue (O-linked glycosylation). N-linked oligosaccharide chains may be multi-antennary, such as, e.g., bi-, tri, or tetra-antennary and most often contain a core structure of $Man_3$-GlcNAc-GlcNAc-.

Both N-glycans and O-glycans are attached to proteins by the cells producing the protein. The cellular N-glycosylation machinery recognizes and glycosylates N-glycosylation consensus motifs (N-X-S/T motifs) in the amino acid chain, as the nascent protein is translocated from the ribosome to the endoplasmic reticulum (Kiely et al. 1976; Glabe et al. 1980).

Some glycoproteins, when produced in a human in situ, have a glycan structure with terminal, or "capping", sialic acid residues, i.e., the terminal sugar of each antenna is N-acetylneuraminic acid linked to galactose via an $\alpha 2 \rightarrow 3$ or $\alpha 2 \rightarrow 6$ linkage. Other glycoproteins have glycans end-capped with other sugar residues. When produced in other circumstances, however, glycoproteins may contain oligosaccharide chains having different terminal structures on one or more of their antennae, such as, e.g., lacking sialic acid residues; containing N-glycolylneuraminic acid (Neu5Gc) residues; containing a terminal N-acetylgalactosamine (GalNAc) residue in place of galactose; and the like. Patterns of N-linked and/or O-linked oligosaccharides may be determined using any method known in the art, including, without limitation: high-performance liquid chromatography (HPLC); capillary electrophoresis (CE); nuclear magnetic resonance (NMR); mass spectrometry (MS) using ionization techniques such as fast-atom bombardment, electrospray, or matrix-assisted laser desorption (MALDI); gas chromatography (GC); and treatment with exoglycosidases in conjunction with anionex-change (AIE)-HPLC, size-exclusion chromatography (SEC), mass spectroscopy (MS), gel electrophoresis (SDS-PAGE, CE-PAGE), isoelectric focusing gels, or iso-electric focusing capillary electrophoresis (CE-IEF) See, e.g., Weber et al., *Anal. Biochem.* 225:135 (1995); Klausen et al., *J. Chromatog.* 718:195 (1995); Morris et al., in *Mass Spectrometry of Biological Materials*, McEwen et al., eds., Marcel Dekker, (1990), pp 137-167; Conboy et al., *Biol. Mass Spectrom.* 21:397, 1992; Hellerqvist, *Meth. Enzymol.* 193:554 (1990); Sutton et al., *Anal. Biohcem.* 318:34 (1994); Harvey et al., *Organic Mass Spectrometry* 29:752 (1994).

The term "terminal sialic acid" or, interchangeable, "terminal neuraminic acid" is thus intended to encompass sialic acid residues linked as the terminal sugar residue in a glycan, or oligosaccharide chain, i.e., the terminal sugar of each antenna is N-acetylneuraminic acid linked to galactose via an $\alpha 2 \rightarrow 3$ or $\alpha 2 \rightarrow 6$ linkage.

The term "galactose or derivative thereof" means a galactose residue, such as natural D-galactose or a derivative thereof, such as an N-acetylgalactosamine residue.

The term "terminal galactose or derivative thereof" means the galactose or derivative thereof linked as the terminal sugar residue in a glycan, or oligosaccharide chain, e.g., the terminal sugar of each antenna is galactose or N-acetylgalactosamine.

The term "asialo glycoprotein" is intended to include glycoproteins wherein one or more terminal sialic acid residues have been removed, e.g., by treatment with a sialidase or by chemical treatment, exposing at least one galactose or N-acetylgalactosamine residue from the underlying "layer" of galactose or N-acetylgalactosamine ("exposed galactose residue").

In general, N-linked glycans can be introduced by introducing amino acid mutations so as to obtain N-X-S/T motifs. The protein molecules of the present invention contains 1, 2, 3, 4, 5, 6, 7, 8, 9, or 10, or more, N-linked glycans. The structure of N-linked glycans are of the high-mannose or complex form. High mannose glycans contain terminal mannose residues at the non-reducing end of the glycan. Complex N-glycans contain terminal sialic acid, galactose or N-acetyl-glucosamine at the non-reducing end.

Likewise, O-glycans are attached to specific O-glycosylation sites in the amino acid chain, but the motifs triggering O-glycosylation are much more heterogenous than the N-glycosylation signals, and the ability to predict O-glycosylation sites in amino acid sequences is still inadequate (Julenius et al. 2004). The construction of artificial O-glycosylation sites is thus associated with some uncertainty.

In the conjugates of the present invention, the side chain is linked to a sialic acid in an N- or O-linked glycan.

Linkage of Hydrophobic Side Groups:

Chemical methods for coupling of groups to proteins tend to be non-selective although some are site-selective. However, common for most methods is the fact that reagents containing hydrophobic groups cannot be employed in aqueous buffers, unless harmful additives such as detergents or organic solvents are added. Hydrophobic groups are inherently difficult to couple to proteins due to their insolubility in aqueous environment, while proteins are only soluble in aqueous environment.

A number of advantages are associated with employment of an enzymatic approach. According to a preferred enzymatic method according to the present invention, [hydrophobic side group]-sialyl-CMP substrates can be prepared chemically. This substrate can be transferred enzymatically to glycans present of asialo proteins using a sialyltransferase enzyme. The inventors of the present invention have surprisingly demonstrated that this enzymatic approach can be performed without addition of organic solvents. A number of disadvantages are associated with use of organic solvents, e.g. loss of biological activity, environmental concerns, additional steps to be taken to ensure that the organic solvents are completely removed, etc. In the handling of FVIII proteins it may be an advantage to add glycerol to buffers, e.g. 5-30% glycerol, preferably 10-20% glycerol. The presence of glycerol seem to stabilize the Factor VIII molecule e.g. in the freeze/thaw process and it may also prevent formation of Factor VIII aggregation. Glycerol is highly hydrophilic and as such not regarded an organic solvent. Furthermore, due to its highly hydrophilic nature, glycerol is devoid of the negative effects on protein stability observed for other organic solvents, such as ethanol, propanol, acetonitrile, dimethylformamide, N-methylpyrrolidine, dimethylsulfoxide, and the like. Glycerol present during enzymatic conjugation does thus not need to be removed after the conjugation process has been completed.

Sialyltransferase: Sialyltransferases are enzymes that transfer a sialic acid to nascent oligosaccharide. Each sialyltransferase is specific for a particular sugar nucleotide donor substrate. Sialyltransferases add sialic acid to the terminal galactose in glycolipids (gangliosides), or N- or O-linked glycans of glycoproteins. There are about twenty different sialyltransferases which can be distinguished on the basis of the acceptor substrate on which they act and on the type of sugar linkage they form. Typically, a linkage is formed between the 2-position of the sialic acid and the 3- or 6-position of the galactose. Preferred sialyltransferases according to the present invention belong to the EC 2.4.99 class of enzymes. Non limiting examples are ST3Gal-I (specific for O-glycans), and ST3Gal-III (specific for N-glycans), and ST6GalNAc-I. It is thus possible to engineer the structure of the conjugated protein according to the present invention by e.g. selection of a specific sialyltransferase and/or engineering of protein with a particular glycosylation pattern.

Acceptor substrate: The term acceptor or acceptor substrate refers to the nucleophilic substrate being linked to a donor substrate by a glycosidic linkage in a sialyltransferase mediated reaction (see eg. Boons and Hale, *Organic Synthesis with Carbohydrates*, Sheffield Academic Press, 2000, Sheffield, England). The acceptor is a mono- or oligosaccharide or a derivative thereof. The reactive part of the acceptor is a hydroxyl-group contained in such mono- or oligo-saccharide or derivative. Typically, the reactive hydroxyl group in a sialyltransferase mediated reaction is a hydroxyl-group on a terminal or non-terminal-galactose. Typically the reactive hydroxyl-group is a 3- or 6-hydroxyl group in a terminal galactose. Another type of reactive hydroxyl group is an 8-hydroxyl group of a terminal sialic acid.

Donor substrate: The term donor or donor substrate refers to the electrophilic substrate being linked to an acceptor substrate by a glycosidic linkage in a sialyltransferase mediated reaction (see eg. Boons and Hale, *Organic Synthesis with Carbohydrates*, Sheffield Academic Press, 2000, Sheffield, England). Donor substrates are sugar nucleotides of the Leloir or non-Leloir type. Preferred sugar nucleotides of the present invention are sialic acid cytidine monophosphates with substituents linked to the N-acetyl group of the sialic acid.

Host cells for producing recombinant proteins are preferably of mammalian origin in order to ensure that the molecule is properly processed during folding and post-translational modification, eg. glycosylation and sulfatation. In practicing the present invention, the cells are mammalian cells, more preferably an established mammalian cell line, including, without limitation, CHO, baby hamster kidney (BHK), and HEK293 cell lines.

Currently preferred cells are HEK293, COS, Chinese Hamster Ovary (CHO) cells, Baby Hamster Kidney (BHK) and myeloma cells, in particular Chinese Hamster Ovary (CHO) cells.

Pharmaceutical composition: A pharmaceutical composition is herein preferably meant to encompass compositions comprising protein molecules according to the present invention suitable for parenteral administration, such as e.g. ready-to-use sterile aqueous compositions or dry sterile compositions that can be reconstituted in e.g. water or an aqueous buffer. The compositions according to the invention may comprise various pharmaceutically acceptable excipients, stabilizers, etc.

Additional ingredients in such compositions may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention. Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the protein in the form of a nasal or pulmonal spray. As a still further option, the pharmaceutical compositions may also be adapted to transdermal administration, e.g. by needle-free injection or from a patch, optionally an iontophoretic patch, or transmucosal, e.g. buccal, administration.

The term "treatment", as used herein, refers to the medical therapy of any human or other animal subject in need thereof. Said subject is expected to have undergone physical examination by a medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Thus, said treatment may be prophylactic, palliative, symptomatic and/or curative.

According to a first aspect, the present invention thus relates to a recombinant protein, wherein said protein is covalently conjugated to at least one hydrophobic side group, wherein said hydrophobic side group is linked to said protein via a sialic acid. The hydrophobic side group is optionally conjugated to the protein via a linker.

In one embodiment, the protein is a coagulation factor such as e.g. FVII (FVII(a)), FVIII, or FIX. In another embodiment, the protein is an antigenic binding fragment of an antibody.

In a preferred embodiment according to the invention, the hydrophobic side group (the "albumin binder") is selected from one or more of the group consisting of: fatty acid and fatty diacid. In another preferred embodiment, the hydrophobic side group is linked to Factor VIII via a sialic acid. In yet another preferred embodiment, the Factor VIII molecule comprises at least one glycan, wherein said at least one glycan is linked to sialic acid and wherein said sialic acid is linked to a hydrophobic side group.

In a particularly interesting embodiment according to the invention, the Factor VIII molecule has modulated, preferably reduced, vWF binding capacity. In yet another interesting embodiment, the Factor VIII molecule is a B-domain truncated variant, preferably comprising a B domain linker having the sequence as set forth in SEQ ID NO 4. According to a particularly preferred embodiment, a hydrophobic side group is covalently conjugated to an O-glycan situated in a truncated B-domain of the Factor VIII molecule, wherein Factor VIII activation results in removal of the hydrophobic side group. In another embodiment, the O-glycan in the B domain is conjugated with a hydrophilic polymer, such as e.g. a PEG, a HES or a PSA or a peptide such as e.g. albumin. If the O-linked glycan in a B domain similar to the B domain set forth in SEQ ID NO 4 is conjugated to a hydrophilic polymer, the one or more hydrophobic side chain is preferably conjugated to an N-linked glycan and vice versa. Hydrophilic polymers can also be conjugated to FVIII via sialic acid on an N-linked and/or an O-linked glycan using either chemical or enzymatic methods. Hydrophilic polymers can also be conjugated to the molecule using other methods known in the art.

In yet another interesting embodiment according to the invention, the Factor VIII polypeptide is fused to another polypeptide such as e.g. an Fc domain (preferably a mutated Fc domain having reduced effector function and/or increased affinity to the neonatal Fc receptor) or an antibody binding protein.

Another aspect relates to methods of making a molecule according to the present invention, wherein said method comprises attachment of a hydrophobic side group to a recombinant Factor VIII molecule. In a preferred embodiment, the hydrophobic side group is attached via a sialyltransferase catalysed reaction. In a particularly preferred embodiment, the sialyltransferase is selected from the group consisting of: ST3Gal-I and ST3Gal-III. In still another embodiment, the sialyltransferase is ST6GalNAc-I. Particularly, the present invention furthermore relates to molecules obtained by or obtainable by such methods. Preferably, the enzymatic methods do not employ any addition of organic solvents, although it may be possible to to add trace amounts (i.e. less than 1%) without significantly reducing efficiency of suchs reactions.

A third aspect relates to a method of treatment of a haemophilic disease, an inflammatory disease, or cancer comprising administering to a patient in need thereof a therapeutically effective amount of a molecule according to the present invention.

A sixth aspect of the invention relates to a protein obtainable by or obtained by a method according to the invention.

A seventh aspect relates to use of a molecule according to the invention for treating haemophilia, inflammatory diseases, and cancer.

A final aspect relates to a pharmaceutical composition comprising a molecule according to the invention.

ABBREVIATIONS

CV=column volumes
FLD=fluorescence detection
MQ=MilliQ water (highly purified water)
m/z=mass to charge ratio
MS=mass spectrometry
HPLC=high pressure liquid chromatography
RP=reversed phase
LC-MS=liquid chromatography-mass spectrometry
NMR=nuclear magnetic resonance spectroscopy
rt or RT=room temperature
Boc=tert butyloxycarbonyl
O-t-Bu=tert butyl ester
t-Bu=tert butyl
CMP=cytidine monophosphate
DCM=dichloromethane, $CH_2Cl_2$, methylenechloride
DIC=diisopropylcarbdiimide
DIPEA=N,N-diisopropylethylamine
DMF=N,N-dimethylformamide
DMSO=dimethylsulfoxide
Fmoc=9H-fluoren-9-ylmethoxycarbonyl
Lys(Mtt)-OH=(S)-6-[(Diphenyl-p-tolyl-methyl)amino]-2-amino-hexanoic acid
Thx=trans-4-aminomethylcyclohexancarboxylic acid
GSC: Glycyl sialic acid CMP ester
MBP: mannose binding protein
NAN=N-acetyl neuraminic acid
NMP=N-methylpyrrolidin-2-one
OEG=(2-[2-(amino)ethoxy]ethoxy)acetic acid
TFA=trifluoroacetic acid
THF=tetrahydrofuran
TIPS=triisopropylsilane
UM=4-Methylumbelliferyl
Lac=lactosyl or lactose
HC: heavy chain
LC: light chain
SC: single chain (HC and LC are covalently connected)
PSC: polyethylene glycol sialic acid CMP ester
wt: wild type Amino acid abbreviations follow IUPAC conventions.

Buffer abbreviations follow Stoll, V. S. and Blanchard, J. S., *Methods of Enzymology*, 182, 1990, Academic Press, 24-38.

EXAMPLES

General Procedures
HPLC

RP-HPLC analysis was performed on a AGILENT® 1100 system using either AGILENT®, ZORBAX® or VYDAC® C18 silica column (typically 4.6 mm×50 mm, 5 μm, 300 Å). Detection was by UV at 214 nm and 280 nm. Elution was performed using a suitable gradient of standard water/0.1% TFA (A) and acetonitrile/TFA (B) buffers.

Preparative RP-HPLC was performed on a Waters system (2545 gradient pump and 2489 detector) or a Gilson system (321 gradient pump, 155 UV/VIS detector and GX-271 liquid handler) using a gradient similar to the analytical system and either a 2 or 5 cm C18 column. In some cases, a neutral system was employed using 10 mM $NH_4HCO_3$ (aq), and 90% acetonitrile with 10% 10 mM $NH_4HCO_3$ (aq) as A- and B-buffers, respectively.

LC-MS

LC-MS analysis was performed on a PE-Sciex API 150 mass spectrometer equipped with two Perkin Elmer Series 200 Micro pumps, a Perkin Elmer Series 200 auto sampler, an Applied Biosystems 785A UV detector. A Waters Xterra 3.0 mm×50 mm 5μ C18 silica column was eluted at 1.5 ml/min at room temperature using the same buffers as for the HPLC system. It was equilibrated with 5% B-buffer, eluted for 1.0 min with 5% B-buffer and then with a linear gradient from 5 to 90% B-buffer over 7 min. Detection was by UV detection at 214 nm and total ion current. A fraction of the column eluate was introduced into the ion spray interface of a PE-Sciex API 100 mass spectrometer. The mass range 100-800 amu was scanned every 2 seconds during the run.

Protein Purification

Protein chromatography was performed on an Äkta Explorer chromatographic system and columns from GE Health Care.

Cyclodextrin-affinity chromatography was performed using a column prepared by immobilising 6-monodeoxy-6-monoamino-beta-cyclodextrin (Sigma product M2314) to an NHS HITRAP® column (GE Healthcare, CV 1 ml, product 17-0716-01) by following the GE Healthcare instruction leaflet 71-7006-00 AT. Chromatography was performed using 20 mM imidazole, 10 mM CaCl2, 150 mM NaCl, pH 7.3, 10% glycerol as starting buffer, and 20 mM imidazole, 10 mM CaCl2, 150 mM NaCl, pH 7.3, 10% glycerol, 20 mM hydroxypropylcyclodextrin as elution buffer.

SDS-PAGE

SDS poly-acrylamide gel electrophoresis was performed using NuPAGE® 7% Trisacetate gels (Invitrogen). The gels were Coomassie® stained (Invitrogen LC6065) or silver stained (SILVERQUEST™ staining kit, Invitrogen)) and where relevant also stained for PEG with barium iodide as described by M. M. Kurfurst in *Anal. Biochem.* 200(2):244-248, 1992.

Samples of FVIII and FVIII-conjugates were optionally treated with thrombin (2 µl, 20 U/ml for every sample 1 µl) prior to LDS treatment. Incubation with thrombin was performed for 10 min at 37° C. Then, the sample was treated according to standard SDS PAGE procedures. In these analyses, a band corresponding to thrombin appeared in the low molecular weight range of the gel.

Protein Concentration Determination

The concentration of FVIII and FVIII-conjugates were determined by UV measurement (A280) with extinction coefficient of 14.6 (1%). Alternatively, where appropriate, an HPLC method was used. The analysis was carried out on an AGILENT®1100 system at 40° C. using a Grace VYDAC® (Mikrolab, Aarhus, Denmark) 214TP5215 C4 column (2.1× 150 mm), particle size 5 mm, with a flow of 200 mL/min. Solvents were 0.07% trifluoroacetic acid (TFA) in Milli-Q water (solvent A) and 0.1% TFA in acetonitrile (solvent B). The Factor VIII protein was eluted with a linear gradient from 40% to 55% solvent B over 60 min. The protein concentration of individual samples were determined by integration of the area on the HPLC chromatogram and comparison to a factor VIII standard. The Factor VIII concentration in the standard was determined by amino acid analysis after hydrolysis in 6N HCl at 110° C. for 24 h. Samples were analysed on a HP1100 HPLC using fluorescence labelling essentially as described by the manufacturer (AGILENT® Technologies, note 5968-5658E).

GSC Starting Material Used in Experiments.

GSC (glycyl sialic acid cytosine 5'-monophosphate ester) was obtained from Albany Molecular Research Inc. in 74% purity according to analytical HPLC (ZORBAX® C18 4.6× 50 mm; A: 10 mM aqueous ammonium bicarbonate; B: 90% acetonitril+10% A; flow: 1 ml/min, gradient: 0-100% B over 16 min, 40° C. oven temperature, UV (214 nm, 280 nm) detection; GSC: Rt=0.5 min).

Example 1

Production of Recombinant B Domain Truncated O-Glycosylated Factor VIII

Cell Line and Culture Process

Using Factor VIII cDNA, a mammalian expression plasmid was constructed. The plasmids encodes a B-domain deleted Factor VIII, the Factor VIII heavy chain comprising amino acid 1-740 of full length human Factor VIII, and Factor VIII light chain comprising amino acid 1649-2332 of full length human Factor VIII (this molecule may herein be referred to as "N8", see Thim et al. Haemophilia (2010) 16, 349). The heavy and light chain sequences are connected by a 21 amino acid linker (SFSQNSRHPSQNPPVLKRHQR—SEQ ID NO 4) comprising the sequence of amino acid 741-750 and 1638-1648 of full length human Factor VIII. Chinese hamster ovary (CHO) cells were transfected with the plasmid and selected with the dihydrofolate reductase system eventually leading to a clonal suspension producer cell cultivated in animal component-free medium.

The first step in the process is the inoculation of a cell vial, from a working cell bank vial, into a chemically defined and animal component free growth medium. Initially after thawing, the cells are incubated in a T-flask. One or two days after thawing, the cells are transferred to a shaker flask, and the culture volume is expanded by successive dilutions in order to keep the cell density between 0.2-3.0×10$^6$ cells/ml. The next step is the transfer of the shaker flask culture into seed bioreactors. The culture volume is here further expanded before the final transfer to the production bioreactor. The same chemically defined and animal component free medium is used for all the inoculum expansion steps. After transfer to the production bioreactor, the medium is supplemented with components that increase the product concentration. In the production bioreactor the cells are cultured in a repeated batch process with a cycle time of three days. At harvest, 80-90% of the culture volume is transferred to a harvest tank. The remaining culture fluid is then diluted with fresh medium, in order to obtain the initial cell density, and then a new growth period is initiated. The harvest batch is clarified by centrifugation and filtration and transferred to a holding tank before initiation of the purification process. A buffer is added to the cell free harvest in the holding tank to stabilise pH.

By the end of the production run, cells are collected and frozen, in order to make an end of production cell bank. This cell bank is tested for *mycoplasma*, sterility and viral contamination.

Purification

For the isolation of B-domain-deleted Factor VIII (Y1680F) from cell culture media a four step purification procedure was used including a concentration step on a CAPTO™ MMC column (i.e., multimodal media), an immunoabsorbent chromatography step, an anionic exchange chromatography and finally a gelfiltration step. Typically the following procedure was used: 11 liter of sterile filtered medium was pumped onto at column (1.6×12 cm) of CAPTO™ MMC (GE Healthcare, Sweden) equilibrated in buffer A: 20 mM imidazole, 10 mM CaCl$_2$, 50 mM NaCl, 0.02% TWEEN® 80 (polysorbate 80), pH=7.5 at a flow of 15 ml/min. The column was washed with 75 ml of buffer A followed by wash with 75 ml of buffer A containing 1.5 M NaCl. The protein was eluted with 20 mM imidazole, 10 mM CaCl$_2$, 0.02% TWEEN® 80, 2.5 M NaCl, 8 M ethyleneglycol, pH=7.5 at a flow of 1 ml/min. Fractions of 8 ml were collected and assayed for Factor VIII activity (Chromogenic assay). Factor VIII containing fractions were pooled and normally a pool volume of around 50 ml was obtained.

A monoclonal antibody against Factor VIII has been developed (Kjalke Eur J Biochem 234 773). By epitope mapping (results not shown) this antibody, F25, was found to recognise the far C-terminal sequence of the heavy chain from amino acid residue 725 to 740. The F25 antibody was coupled to NHS-activated SEPHAROSE®4 FF (gel filtration medium) (GE Healthcare, Bio-Sciences AB, Uppsala, Sweden) at a density of 2.4 mg per ml of gel essentially as described by the manufacturer. The pool from the previous step was diluted 10 times with 20 mM imidazole, 10 mM CaCl$_2$, 0.02% TWEEN® 80, pH=7.3 and applied to the F25 SEPHAROSE® column (1.6×9.5 cm) equilibrated with 20 mM imidazole, 10 mM CaCl$_2$, 150 mM NaCl, 0.02% TWEEN® 80, 1 M glycerol pH=7.3 at a flow of 0.5 ml/min. The column was washed with equilibration buffer until the UV signal was constant and then with 20 mM imidazole, 10 mM CaCl$_2$, 0.65 M NaCl, pH=7.3 until the UV signal was constant again. Factor VIII was eluted with 20 mM imidazole, 10 mM CaCl$_2$, 0.02% TWEEN® 80, 2.5 M NaCl, 50% ethyleneglycol, pH=7.3 at a flow of 1 ml/min. Fractions of 1 ml were collected and assayed for Factor VIII activity (Chromogenic assay). Factor VIII containing fractions were pooled and normally a pool volume of around 25 ml was obtained.

A buffer A: 20 mM imidazole, 10 mM CaCl$_2$, 0.02% TWEEN®80, 1 M glycerol, pH=7.3 and a buffer B: 20 mM imidazole, 10 mM CaCl$_2$, 0.02% TWEEN®80, 1 M glycerol, 1 M NaCl, pH=7.3 was prepared for the ion-exchange step. A column (1×10 cm) of MACROPREP® 25Q (i.e., ion exchange) Support (Bio-Rad Laboratories, Hercules, Calif., USA) was equilibrated with 85% buffer N15% Buffer B at a flow of 2 ml/min. The pool from the previous step was diluted 10 times with buffer A and pumped onto the column with a flow of 2 ml/min. The column was washed with 85% buffer N15% buffer B at a flow of 2 ml/min and Factor VIII was eluted with a linear gradient from 15% buffer B to 70% buffer B over 120 ml at a flow of 2 ml/min. Fractions of 2 ml were collected and assayed for Factor VIII activity (Chromogenic assay). Factor VIII containing fractions were pooled and normally a pool volume of around 36 ml was obtained.

The pool from the previous step was applied to a SUPERDEX®200 (gel filtration media), prep grade (GE Healthcare, Bio-Sciences AB, Uppsala, Sweden) column (2.6×60 cm) equilibrated and eluted at 1 ml/min with 20 mM imidazole, 10 mM $CaCl_2$, 0.02% TWEEN®80, 1 M glycerol, 150 mM NaCl, pH=7.3. Fractions of 3 ml were collected and assayed for Factor VIII activity (Chromogenic assay). Factor VIII containing fractions were pooled and normally a pool volume of around 57 ml was obtained. The pool containing Factor VIII was store at −80° C.

With the use of the above four-step purification procedure an overall yield of approximately 15% was obtained as judged by Chromogenic activity and ELISA measurements.

The recombinant N8 Factor VIII molecule obtained in Example 1 has one O-linked glycan present in the B-domain (see Thim et al. Haemophilia (2010) 16, 349). Specific attachment of a hydrophobic side group to this O-glycan thus enables production of a molecule having a homogenous structure. Furthermore, upon activation of the molecule, the B-domain and the hydrophobic side chain is removed and the activated molecule therefore has a structure that is similar to activated endogenous Factor VIII.

Example 2

Coupling of C-16 Fatty Diacid γ-Glu NHS Ester to GSC to Yield Sialyltransferase Substrate 1

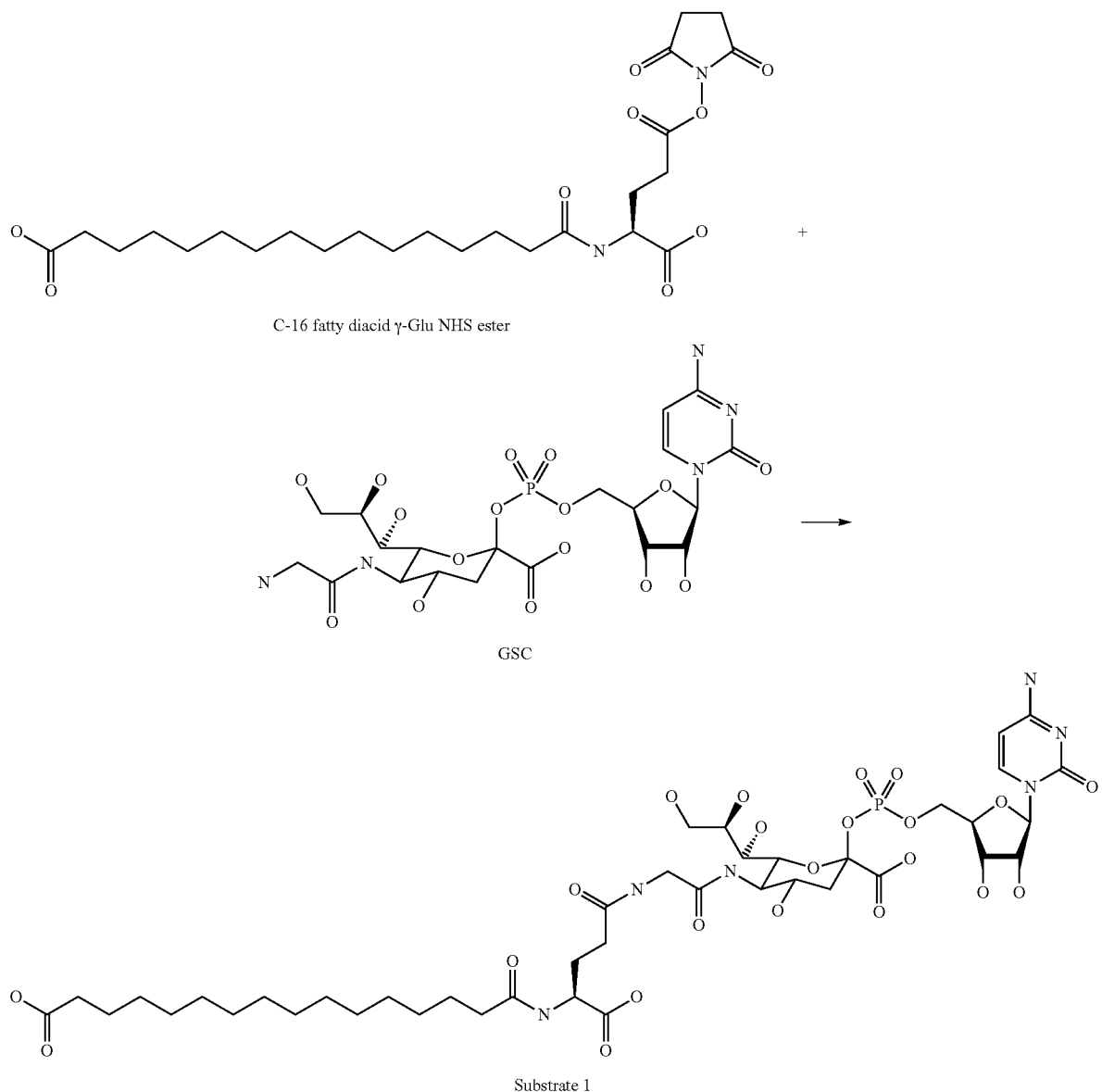

C-16 fatty diacid γ-Glu NHS ester

GSC

Substrate 1

GSC (Glycyl sialic acid CMP ester) (7.5 mg, 11 μmol) was dissolved in a mixture of TRIS buffer (100 mM, pH 8.4, 50 μl) and aceonitrile 50 μl. A two-phase system was obtained. The C-16 fatty diacid γ-Glu NHS ester (7 mg; for preparation of the analogous C-18 compound see WO 2005/012347 A2 example 5) was dissolved in THF (50 μl), then TRIS-buffer (50 μl) was added to obtain a clear solution. This solution was added to the solution of GSC. A clear solution was obtained. After approximately 4 h reaction time, the sample was concentrated in vacuo to remove the bulk of organic solvents and then frozen at −20° C. The product (1) was identified by HPLC and LC-MS.

Purification by RP-HPLC using the neutral buffer system and a C4 Jupiter 10×250 cm column. Flow 5 ml/min, gradient 2% B-buffer/min. A late eluting fraction containing the product 1 was collected. The fraction was concentrated to dryness. Despite the relatively good retension on the C4 column, the product displayet full water solubility and was redissolved in 10 mM NH$_4$HCO$_3$. The concentration of the product in the solution was determined to 4.1 μM by UV measurement at 272 nm (CMP group) using GSC as a standard. Yield 4.2 mg (50%). The product identity was confirmed by LCMS. The product solution was stored at −20° C. Using the above protocol, a sialyl transferase substrate carrying a hydrophobic side chain was prepared. The substrate 1 proved to be fully soluble in aqueous buffer.

Example 3

Preparation of Albumin Binder NHS Ester 2

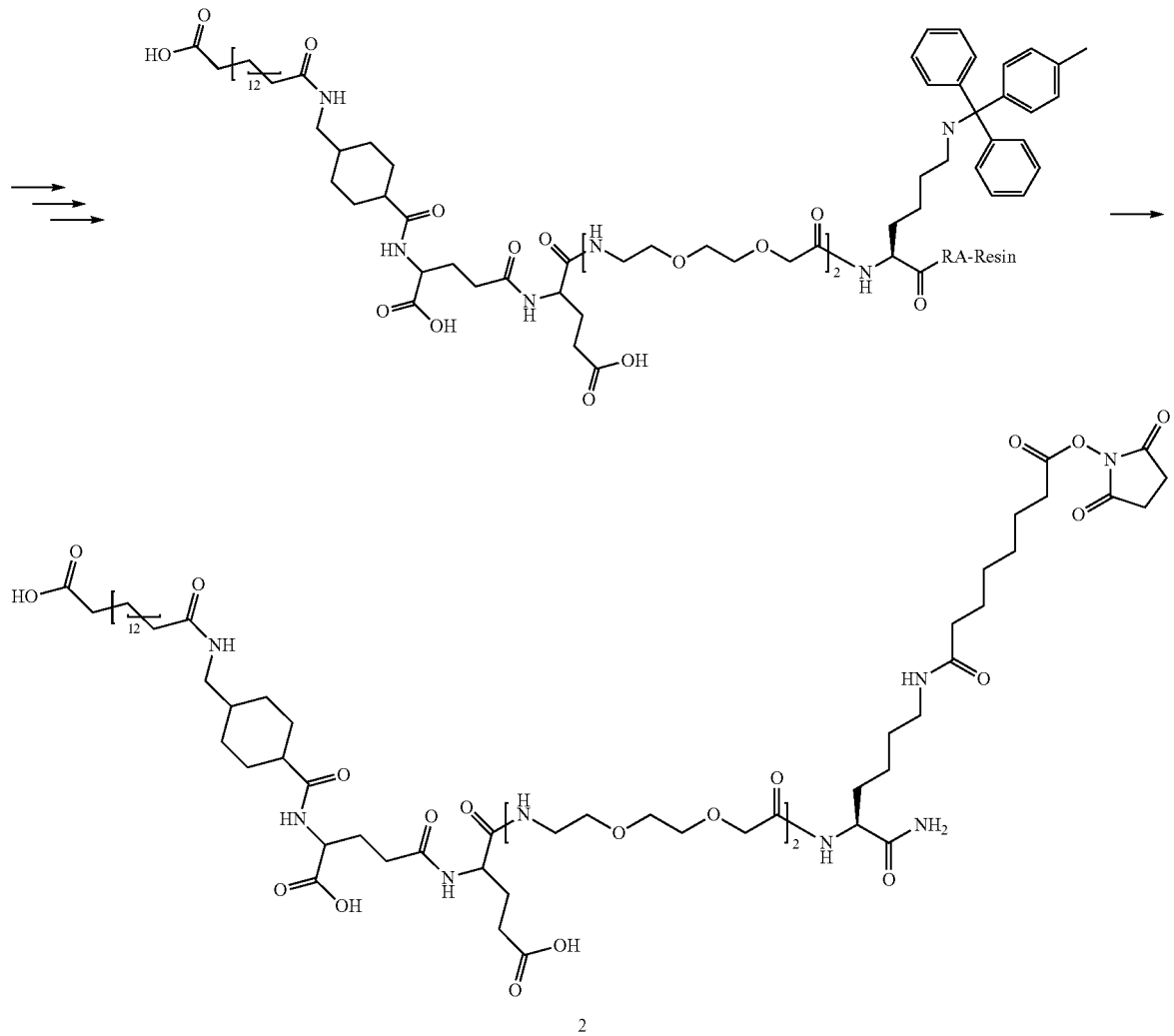

Rink-Amide resin (Novabiochem, 0.4 g, 0.25 mmol) was used for synthesis on a CEM Liberty microwave peptide synthesizer. Standard Fmoc chemistry protocols were used with the following amino acids being used and in that order (all solutions with 7 eq. of amino acid in NMP containing 0.3 M HOAt):

1. Fmoc-Lys(Mtt)-OH: 1.12 g in 6 ml
2. Fmoc-OEG-OH: 1.39 g in 12 ml (2 couplings)
3. Fmoc-Glu-OtBu: 0.77 g in 6 ml
4. Fmoc-Thx-OH: 0.68 g in 6 ml
5. C-16 diacid mono t-butylester (see WO 2005/012347 A2 example 4): 0.62 g in 6 ml All couplings were performed by adding DIC 7 eq.

After these couplings, the resin was removed from the Liberty synthesizer and was washed, drained, and treated with 5 ml hexafluoro isopropanol for 10 minutes. The resin was then washed with DCM and drained. Then, the hexafluoro isopropanol treatment and DCM washing was repeated.

Suberic acid bis-NHS ester (368 mg) was dissolved in NMP (10 ml, with 0.5 mM bromophenol blue) and DIPEA (170 µl) was added. This solution was added to the drained resin and allowed to react overnight. After the coupling, the resin was washed with NMP, then DCM and drained. To the drained resin, a mixture of TFA:TIPS:Mercaptoethanol:H2O 94:1:2.5:2.5 was added and the resin was shaken at ambient temperature for 2 hours. The resin was drained slowly into 75 ml ice-cooled diethyl ether resulting in precipitation of the product. Further stirring at rt. for 0.5 hour and centrifugation yielded the product as a solid which was washed twice with diethylether and dried in vacuo. The crude product was dissolved in a mixture of HPLC A- and B-buffers, and purified by preparative RP-HPLC. Product identity and purity was confirmed by HPLC and LCMS.

Using the above protocol, a highly complex albumin binding side chain was prepared as an NHS ester. This compound is set up to react with GSC in example 4.

Example 4

Coupling of the NHS Ester to GSC to Yield Substrate 3

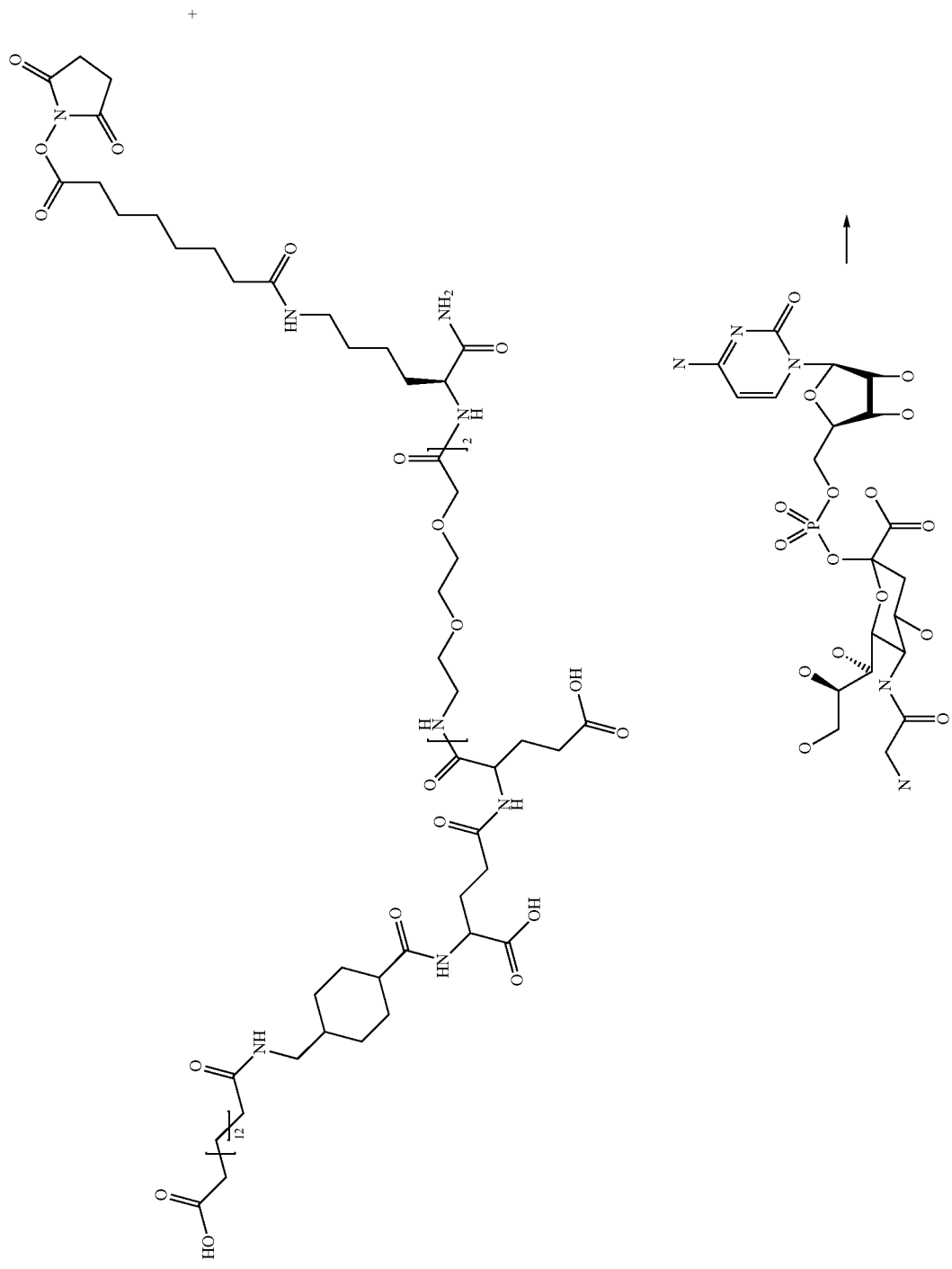

-continued
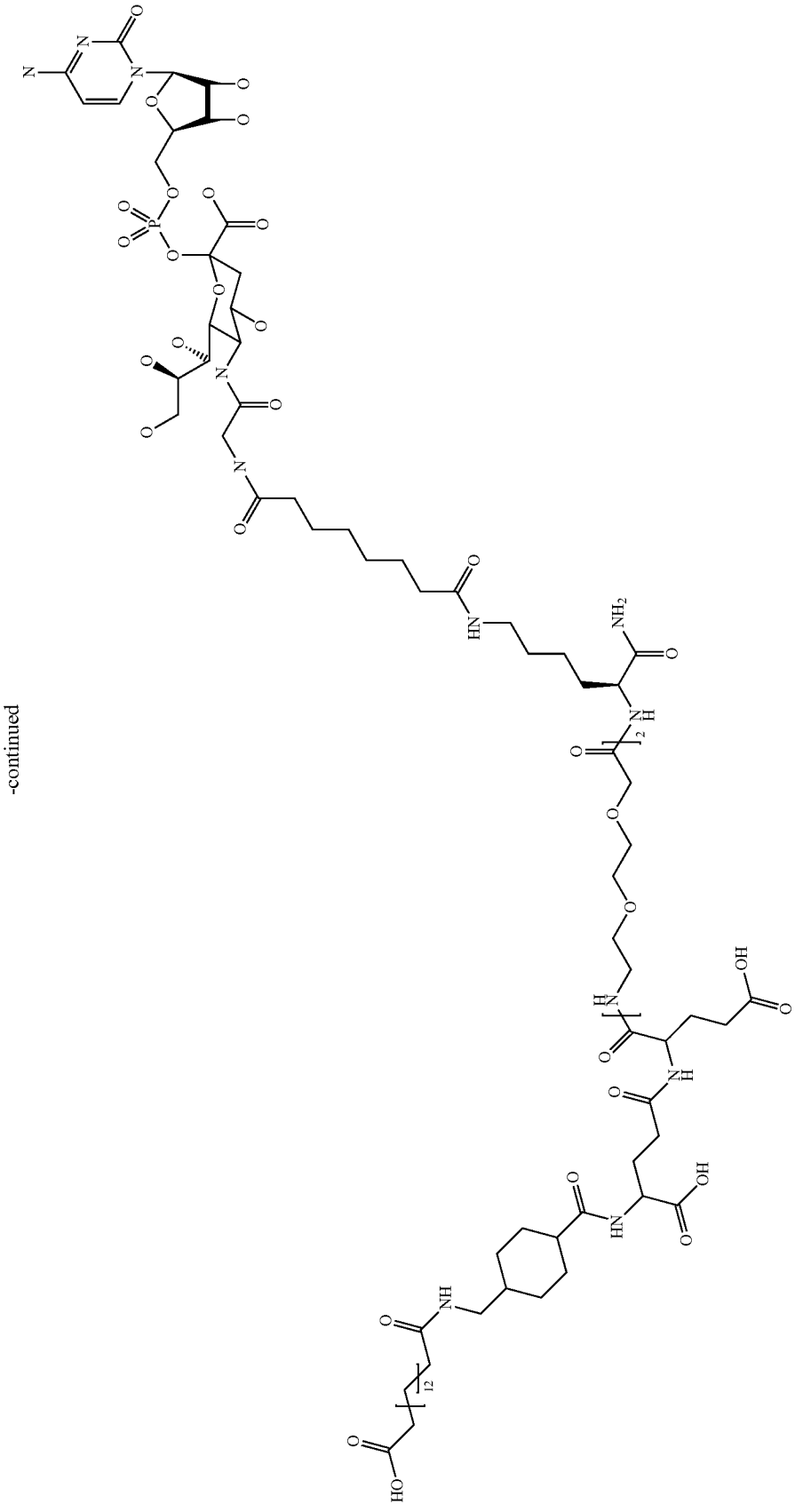

The NHS ester 2 of Example 3 (20 mg) was dissolved in THF (500 µl) and TRIS buffer (100 mM, pH 8.4, 1500 µl) was added. GSC (20 mg) was weighed out and added to the solution of NHS-ester and allowed to react at rt. for a period of 30 min. The reaction mixture was diluted to 4 ml with MO-water and purified by RP HPLC as outlined in Example 2. Gradient 10→50% B-buffer. Relevant fractions were identified by LCMS and freezedried. Again, the product showed excellent water-solubility. Yield: 7.7 mg. The product was identified by LCMS.

Using the above protocol, a sialyltransferase substrate carrying a complex albumin binding hydrophobic side chain was prepared. The substrate 3 proved to be fully soluble in aqueous buffer.

Example 5

Coupling of Substrate 1 to Fluorescently Labelled Lactose

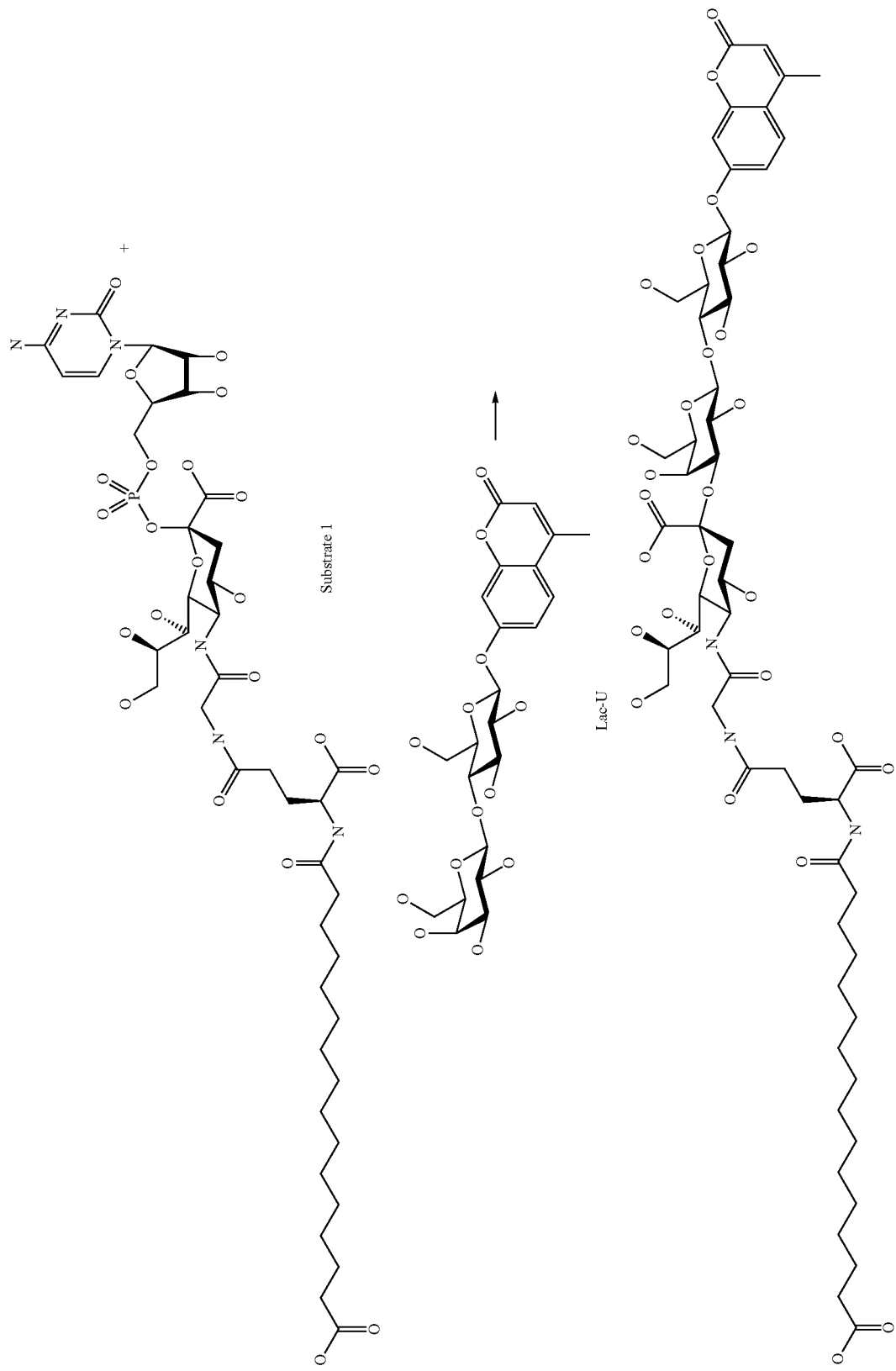

Reagents used for the reaction:

Buffer: HEPES 100 mM, pH 7.5

Enzyme: α2,3-(N)-sialyltransferase, Rat, rec., from CalBiochem, cat. no. 566218. The enzyme was diluted in buffer and concentrated approximately 10 times in a 10 kDa Millipore BIOMAX® polyethersulfone polypropylene ultrafiltration device: 100 µl was dispensed into each of two devices and centrifuged at 12.000 G for 2+6 min at r.t. Final volume approximately 8-10 µl (each) and conc of 1700 mU/ml. 12.5 mU, 7.5 µl was used for the reaction.

Acceptor: Lac-UM. Solution 0.5 mg/ml (1 mM) in TRIS 50 mM, pH 7.4+1 mM $CaCl_2$. A volume of 2.5 µl (2.5 nmol) was used in each reaction Donor, substrate 1: 12.5 nmol, 3 µl was used in each reaction Control donor, CMP-NAN, 1.4 mg, ie. 2.2 µmol/540 µl HEPES pH 7.5: 4.1 mM. 12.5 nmol was used in each reaction, ie. 3 µl Two reactions were carried out in Eppendorf tubes and was followed by RP HPLC. The following HPLC method was used: column C18 2.1×50 mm, Buffers: A: neat water, B: neat MeCN, Flow: 0.2 ml/min, Column temperature: 40° C. Detection UV: 214 and 254 nm, FLD: Exc: 315 nm, emm: 375 nm. The reactions were quantified by following the FLD trace.

Reaction 1: acceptor+donor+enzyme. The reaction reached 81% conversion to the product after a period of 20 h. The product was confirmed by LCMS.

Reaction 2: acceptor+control donor+enzyme. The reaction reached 97% conversion to the product after a period of 20 h.

A control reaction without enzyme gave no product formation after 20 h.

This reaction was used to verify the ability of substrate 1 to react as donor in a sialyltransferase catalysed coupling reaction with fluorescently labelled lactose (Gal-Glc, which is a mimic of the terminal GalNAc-Glc di-saccharide on asialoprotein glycans) as acceptor. All reactions were carried out in aqueous buffers.

Example 6

Coupling of C18-Fatty Diacid γGlu-OEG-OEG NHS Ester to GSC to Yield Sialyltransferase Substrate 4

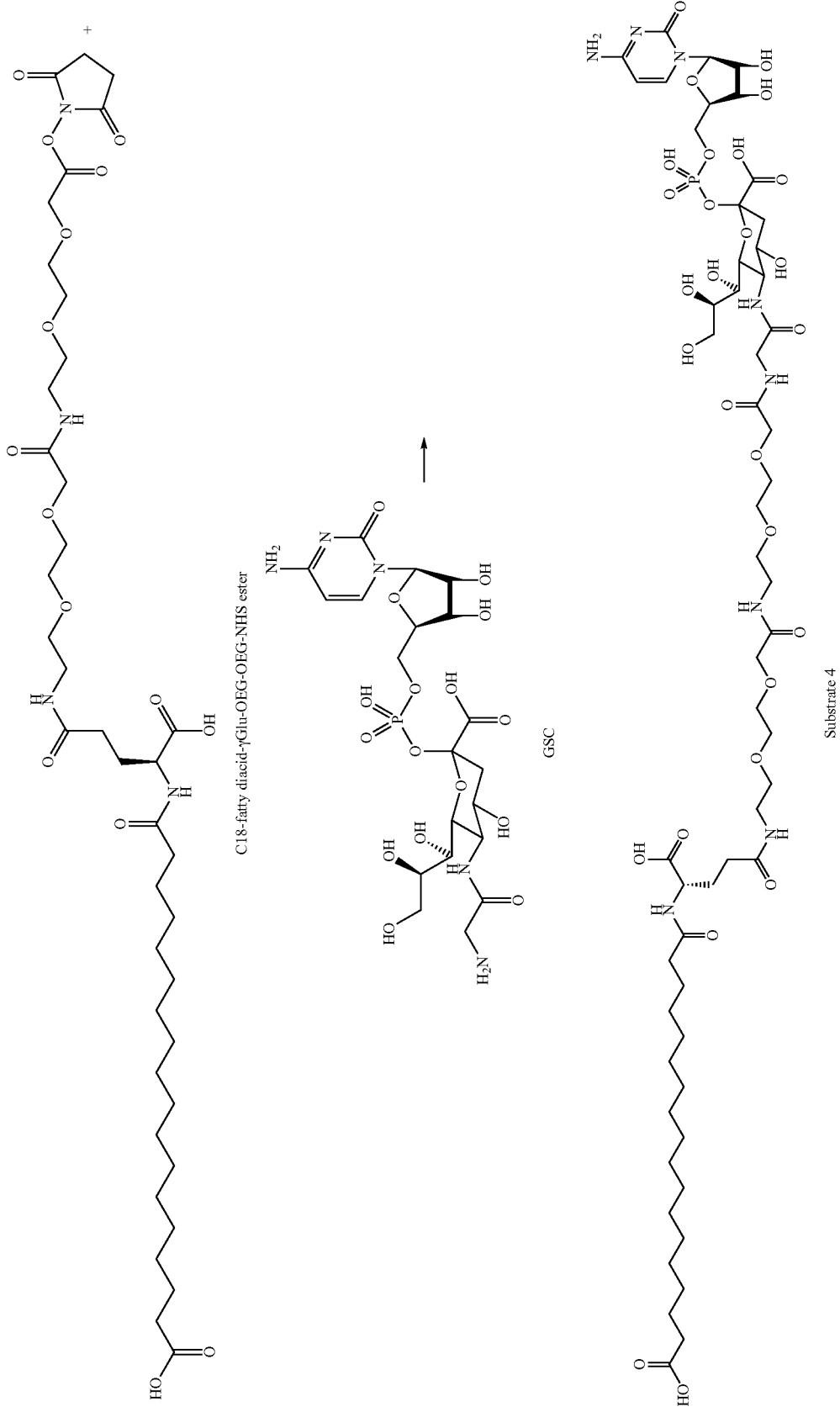

17-((S)-1-Carboxy-3-{2-[2-({2-[2-(2,5-dioxo-pyrrolidin-1-yloxycarbonylmethoxy)ethoxy]ethylcarbamoyl}methoxy)ethoxy]ethylcarbamoyl}propylcarbamoyl)heptadecanoic acid (300 mg; 0.36 mmol, for the preparation of this compound see WO 2009/115469 A1) was dissolved in a mixture of THF (6 ml) and 100 mM HEPES buffer pH 7.5 (4.5 ml). A solution of GSC (glycyl sialic acid cytosine 5'-monophosphate ester, 252 mg; 0.397 mmol) in a mixture of THF (4.5 ml) and 100 mM HEPES buffer pH 7.5 (6 ml) was added. Reaction mixture was incubated for 1 h. HPLC showed complete conversion of GSC starting material. Reaction mixture was purified by several runs on preparative HPLC (C18 50×200 mm; A: water; B: acetonitril; C: 100 mM aqueous ammonium bicarbonate; flow: 50 ml/min; gradient: 90(A):0(B):10(C) isocratic for 8 min, then chance linearly to 60(A):30(B):10(C) over 40 min; Substrate 4: $R_t$=36 min). Fractions were analyzed by analytical HPLC. Pure fractions were pooled and lyophilized to remove ammonium bicarbonate. Ammonium counter ions were exchanged with sodium cations by dissolving the lyophilized powder in water and passing it through a short column of DOWEX® 50W X2 (fine mesh resin)—in its sodium form. The aqueous eluate was once more lyophilized to give a total of 278 mg of substrate 4. LC-MS (electrospray) API3000 (300-2000): Rt=3.98 min, m/z=1345. $^1$H-NMR (DMSO; 400 MHz; selected peaks): δ 1.22 ppm (bs; 28H); 1.40 (bs, 4H); 1.72 (m, 1H); 1.86 (m, 1H); 2.07 (m, 4H); 5.75 (m, 2H); 6.77 (bs, 1H); 7.02 (bs, 1H); 7.23 (bs, 1H); 7.55 (m, 1H); 7.68 (m, 1H); 7.95 (s, 1H); 8.48 (s, 1H).

Example 7

Coupling of Substrate 3 to Fluorescently Labelled Lactose

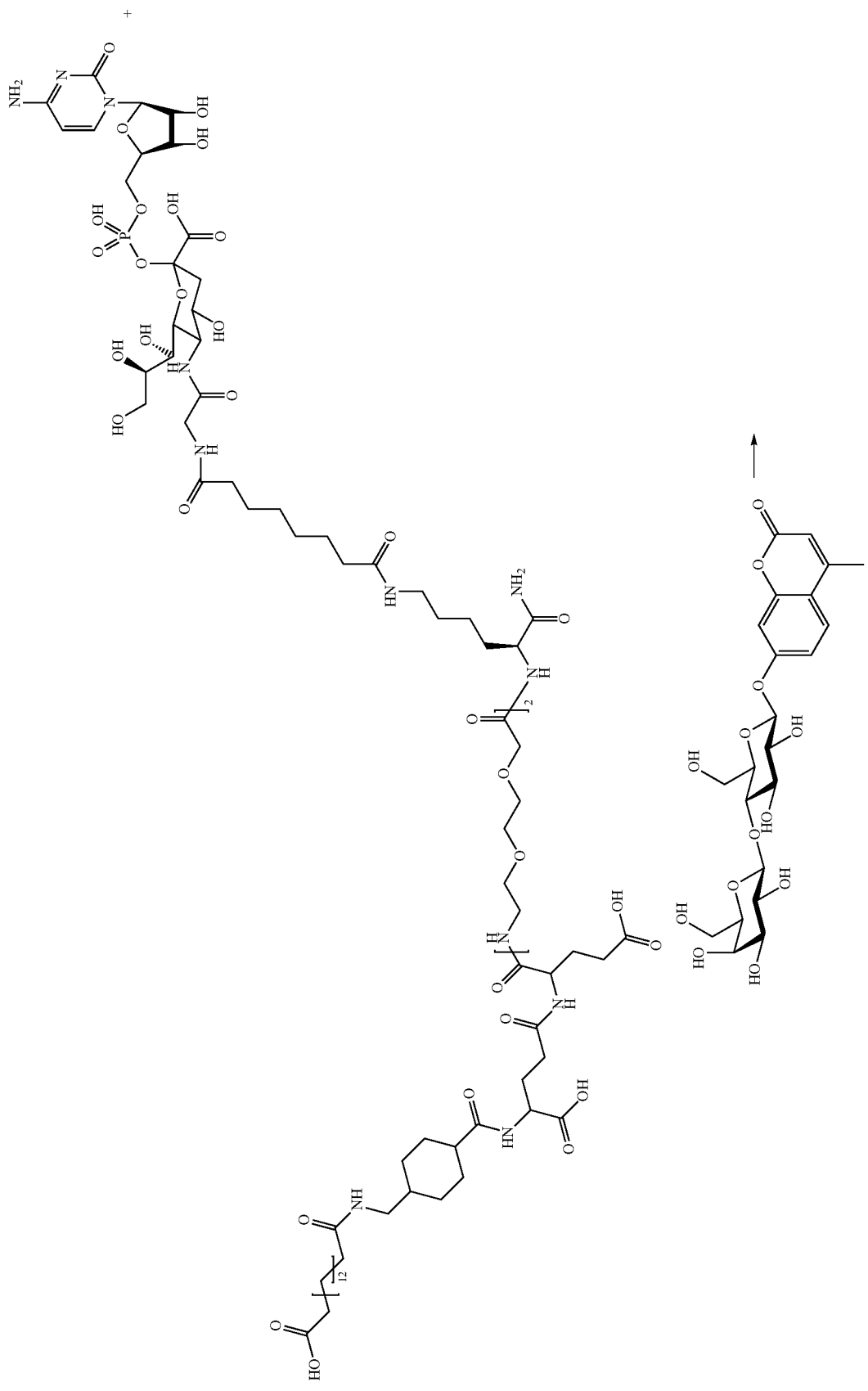

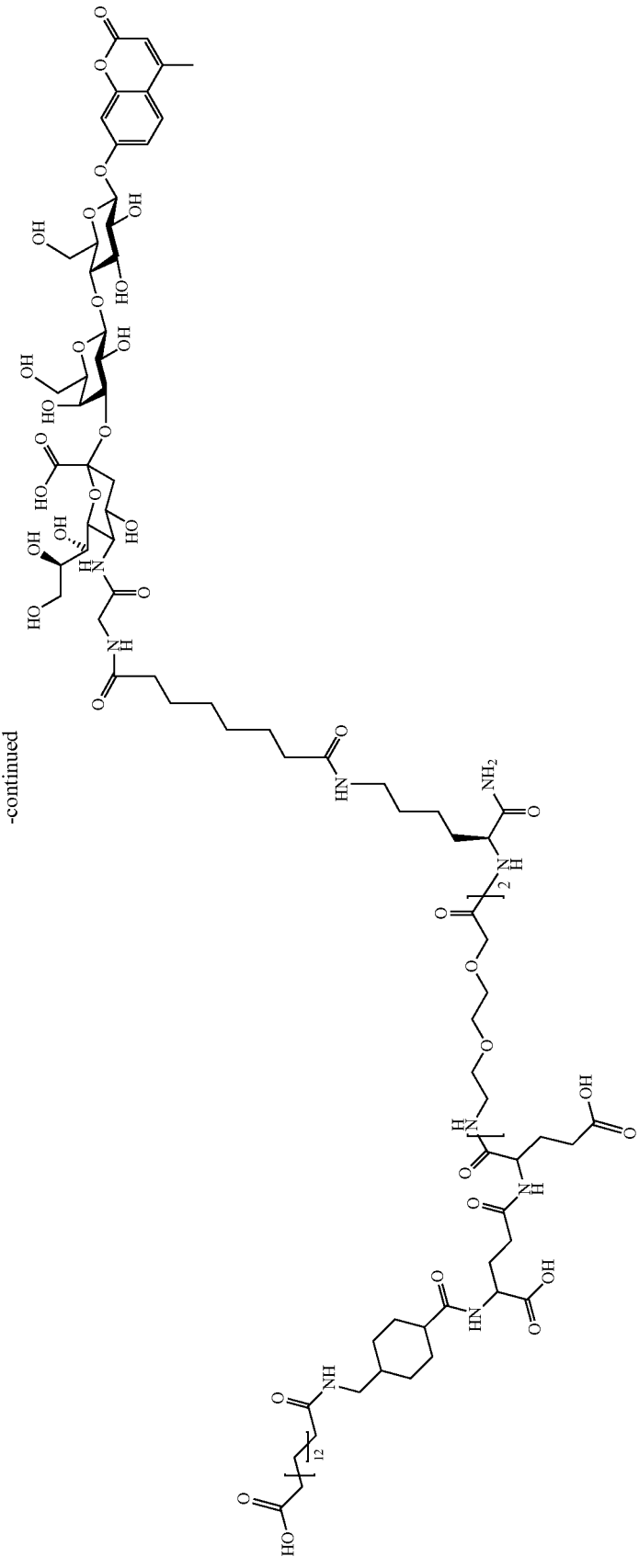

Acceptor: Lac-UM, Solution 0.5 mg/ml (1 mM) in TRIS-buffer (50 mM, pH 7.4+1 mM $CaCl_2$). 2.5 µl (2.5 nmol) was used in each reaction Enzyme: rat MBP-ST3Gal-III, 1.06 U/mg; 0.9 mg/ml. (0.954 mU/µl). 2.6 µl (2.5 mU) was used in each reaction (for a reference to the enzyme, see eg. U.S. Pat. No. 7,220,555 B2)

Donor, substrate 3: 2.5 µg/µl in imidazole-buffer, 10 µl (13.4 nmol) was used in each reaction Control donor: CMP-NAN, 1.4 mg, 4.1 mM HEPES buffer Reaction 1: Acceptor (2.5 µl)+Donor (10 µl)+Enzyme (2.6 µl)

Reaction 2: Acceptor (2.5 µl)+Control-donor (4 µl)+Enzyme (2.6 µl)

Reaction 3: Acceptor (2.5 µl)+Donor (10 µl) (no enzyme)

Three reactions were carried out in eppendorf tubes, the acceptor+donor+enzym were mixed and incubated at 37° C.

The reactions were monitored by HPLC, using the following HPLC method: Column: C18 2.1×50 mm, Buffers: A: 0.1% TFA in Water, 1: 0.1% TFA in MeCN, Flow: 0.2 ml/min, Column temperature: 40 C, DAD: 214 and 254 nm, FLD: Exc: 315 nm, emm: 375 nm Results:

Reaction 1: almost fully converted to product after 2 hours.
Reaction 2: fully converted to product after 1 hour.
Reaction 3: no reaction
Products were identified by LCMS This reaction was used to verify the ability of substrate 3 to react as donor in a sialyltransferase catalysed coupling reaction with fluorescently labelled lactose (Gal-Glc, which is a mimic of the terminal GalNAc-Glc di-saccharide on asialo-protein glycans) as acceptor. All reactions were carried out in aqueous buffers.

Example 8

Coupling of Substrate 1 to the N-Glycans of Wt B-Domain Deleted FVIII ("N8") Using ST3Gal-III wt B-domain deleted FVIII: 0.3 mg in 150 µl buffer (20 mM imidazole, 10 mM $CaCl_2$, 0.02% TWEEN®80, 500 mM NaCl, 1 M glycerol, pH 7.3)

Sialidase/Neuraminidase: 60 µl (ca 72 mU) (*C. perfringens*, type VI-A, N-5254 from Sigma, 0.6-1.8 U/ml gel) on agarose (suspension)

Substrate 1: 4 µl, 4.1 mM, 16 nmol, in 10 mM $NH_4HCO_3$

ST3Gal-III: 300 µl (0.9 mg/ml). Same batch as used in example 7

|  | MW/activity | amount |
| --- | --- | --- |
| FVIII | 178.400 Da | 0.15 mg, 0.84 nMol |
| Sialidase | 0.6-1.8 U/ml gel | 60 ml, ca 72 mU |
| Substrate 1 | 4.1 mM | 20 nmol |
| ST3Gal-III | 0.9 mg/ml; 1.06 U/mg | 300 mU, ca 95 mU |

The sialidase was washed in a mini-filtering device for centrifugation (PIERCE®): twice with water 2×200 µl, then three times with buffer (HEPES, 100 mM pH 7.5). Finally, it was drained. FVIII (0.3 mg in approximately 150 µl buffer) was added and mixed. Every 15 minutes the reaction was mixed with a pipette. After 3 hours reaction, the mixture was filtered and a sample was taken for SDS PAGE analysis. Half the filtrate was used for further reaction (70 µl). ST3Gal-III (300 µl) was concentrated to ca 30 µl using a 10 kDa Millipore B10-MAX® ultrafiltration device: 12.000 g for ca 6 min). Substrate 1 (4 µl) and ST3Gal-III (10 µl of the concentrated material) were added to the filtrate. The mixture was incubated at 32° C. Samples were taken for SDS PAGE after 1 hour and after 23 hours.

SDS PAGE analysis of samples (non-reduced)

1 µl sample was diluted with 100 µl FVIII buffer. 2×25 µl were taken from each sample for analysis with or without prior treatment with thrombin.

The gel was stained by SILVERQUEST™

Lanes (2-5 and 7-12 were with and without thrombin treatment, respectively):

2: wt B-domain deleted FVIII: two bands intense corresponding to HC and LC, one less intense band corresponding to SC 3: Reaction mixture after 3 h with sialidase: identical to lane 1.

4 and 5: Reaction mixture after 1 h and 23 h with substrate 1 and ST3Gal-III: Identical to lane 2, but with additional bands corresponding to ST3-Gal-III.

7: wt B-domain deleted FVIII: a series of bands corresponding to LC' (A3C1C2 domains), A1 and A2.

8: Reaction mixture after 3 h with sialidase: identical to lane 7

9 and 10: Reaction mixture after 1 h and 23 h with substrate 1 and ST3Gal-III. Very similar to lanes 7 and 8, but of note the A1 and A3C1C2 bands had shifted slightly towards higher MW corresponding to the modification with the fatty acid moiety of substrate 1.

The SDS-PAGE gel analysis provided evidence for attachment of 1-4 groups C16-gammaGlu-sialic acid onto the asialo-N-glycans of wt B-domain deleted FVIII.

This example shows that substrate 1 can be coupled to FVIII. Surprisingly, the highly hydrophobic, fatty acid-containing substrate was freely water soluble and easy to handle in buffers.

Example 9

Preparation of N-Glycan Modified Wt B-Domain Deleted FVIII ("N8") by Reaction with Substrate 1 and ST3Gal-III: Compound 5

Asialo wt B-domain deleted FVIII (1 mg, 5.6 nmol, in 800 µl buffer histidine (1.5 mg/ml), $CaCl_2$ (0.25 mg/ml), TWEEN®80 (0.1 mg/ml), NaCl (500 mM), sucrose (3 mg/ml) was treated with ST3Gal-III (500 µl, conc. to 50 µl, 500 mU) and substrate 1 (20 µl, 80 nmol). The reaction was incubated at 32° C. for 22 h. A sample was withdrawn for SDS PAGE analysis. Then, a solution of CMP-NAN (2 mg, 3.1 µmol in 20 µl buffer (20 mM imidazole, 10 mM $CaCl_2$, 0.02% TWEEN®80, 500 mM NaCl, 1 M glycerol, pH 7.3)) was added and incubated at 32° C. for 1 h.

The reaction mixture was diluted to 19 ml with approximately 18 ml 20 mM imidazole, 10 mM $CaCl_2$, 0.02% TWEEN®80, 1 M glycerol, pH 7.3. The salt concentration was then approximately 28 mM. The solution was loaded to a spin AIEC conlumn (Vivapure Q Mini M, strong anion exchange) which had been equilibrated with 10 ml 20 mM imidazole, 10 mM $CaCl_2$, 0.02% TWEEN®80, 1 M glycerol, pH 7.3. Then, the column was washed with 1. 2×10 ml of 20 mM imidazole, 10 mM $CaCl_2$, 0.02% TWEEN®80, 1 M glycerol, pH 7.3, 2. 2×10 ml of 20 mM imidazole, 10 mM $CaCl_2$, 0.02% TWEEN®80, 1 M glycerol, pH 7.3, 50 mM NaCl 3. 2×10 ml of 20 mM imidazole, 10 mM $CaCl_2$, 0.02% TWEEN®80, 1 M glycerol, pH 7.3, 200 mM NaCl.

Finally, the FVIII conjugate was eluted with 20 mM imidazole, 10 mM $CaCl_2$, 0.02% TWEEN® 80, 1 M glycerol, pH 7.3, 1 M NaCl. The conjugate (700 µg) was recovered in 1 ml.

It was applied to a SUPERDEX®200 10/300 GL gelfiltration column and eluted with histidine (1.5 mg/ml), CaCl$_2$ (0.25 mg/ml), TWEEN®80 (0.1 mg/ml), NaCl (18 mg/ml), sucrose (3 mg/ml). The eluate contained one peak at approximately 0.4 column volumes and another peak at approximately 0.60 column volumes. The first peak was identified by SDS PAGE as being ST3Gal-III enzyme (probably in an aggregated form). The second peak contained the conjugate (5), isolated as 226 µg in 3.5 ml. The product was characterised by non-reduced SDS PAGE with prior thrombin cleavage, according to which the bands corresponding to A1 and A3C1C2 containing the modified glycans were shifted slightly towards higher MW. In this example, substrate 1 was coupled to the N-glycans of FVIII and the conjugate was isolated by chromatographic steps. The coupling was easily performed.

Example 10

Preparation of N-Glycan Modified Wt B-Domain Deleted FVIII by Reaction with Substrate 3 and ST3Gal-III: Compound 6

Asialo wt B-domain deleted FVIII (1 mg, 5.6 nmol, in 800 µl buffer histidine (1.5 mg/ml), CaCl$_2$ (0.25 mg/ml), TWEEN®80 (0.1 mg/ml), NaCl (500 mM), sucrose (3 mg/ml) was treated with ST3Gal-III (500 µl, conc. to 50 µl, 500 mU) and substrate 3 (45 µl, 60 nmol). The reaction was incubated at 32° C. for 21.5 h. A sample was withdrawn for SDS PAGE analysis. Then, a solution of CMP-NAN (2 mg, 3.1 µmol in 20 µl buffer (20 mM imidazole, 10 mM CaCl$_2$, 0.02% TWEEN®80, 500 mM NaCl, 1 M glycerol, pH 7.3)) was added and incubated at 32° C. for 1 h.

The reaction mixture was diluted to 19 ml with ca 18 ml 20 mM imidazole, 10 mM CaCl$_2$, 0.02% TWEEN®80, 1 M glycerol, pH 7.3. The salt concentration was then ca 28 mM. The product was then purified by spin column AIEC as outlined in example 9. The conjugate (820 µg) was recovered in 1 ml. It was applied to a SUPERDEX®200 10/300 GL gelfiltration column and eluted with histidine (1.5 mg/ml), CaCl$_2$ (0.25 mg/ml), TWEEN®80 (0.1 mg/ml), NaCl (18 mg/ml), sucrose (3 mg/ml). The eluate contained one peak at approximately 0.43 column volumes and another peak at approximately 0.58 column volumes. The first peak was identified by SDS PAGE as being ST3Gal-III enzyme (probably in an aggregated form). The second peak contained the conjugate (6), isolated as 273 µg in 2.5 ml. The product was characterised by non-reduced SDS PAGE with prior thrombin cleavage, according to which the bands corresponding to A1 and A3C1C2 containing the modified glycans were clearly shifted towards higher MW.

In this example, substrate 3 was coupled to the N-glycans of FVIII and the conjugate was isolated by chromatographic steps.

Example 11

Preparation of O-Glycan Modified Wt B-Domain Deleted FVIII by Reaction with Substrate 3 and ST3Gal-I: Compound 7 wt B-domain deleted FVIII (5.7 mg/ml, 352 µl, 10.2 nmol) in buffer (20 mM imidazole, 10 mM CaCl$_2$, 0.02% TWEEN®80, 1 M glycerol, pH 7.3, 500 mM NaCl) was mixed with sialidase (*A. ureafaciens*, 12 µl, 0.43 mg/ml, 130 U/ml, see Christensen and Egebjerg, *Biotechnol. Appl. Biochem.*, 41, 225-231), HIS-ST3Gal-I (21.6 U/mg, 100 µl) and substrate 3 (150 µl, 200 nmol). The mixture was incubated at 32° C. for 2.5 h after which the conjugated FVIII was isolated by cyclodextrin-affinity chromatography. The material was loaded to the immobilsed cyclodextrin column and washed with 18 ml of starting buffer. The elution was performed as a step to 100% elution buffer whereby the product eluted as 730 µg in 2.5 ml. The product was then treated with CMP-NAN (40 µl, 34 mg/ml) and MBP-SBD-ST3Gal-III (200 µl, 0.33 mg/ml, approximately 0.5 U/ml) at 32° C. for 1 h, and frozen. After thawing, the product was purified by spin column AIEC as outlined in example 9 and the final elution was performed with 5×350 µl of 20 mM imidazole, 10 mM CaCl2, 0.02% TWEEN®80, 1 M glycerol, pH 7.3, 1 M NaCl giving the conjugate 586 µg in 700 ul. It was applied to a SUPERDEX®200 10/300 GL gelfiltration column and eluted with histidine (1.5 mg/ml), CaCl$_2$ (0.25 mg/ml), TWEEN®80 (0.1 mg/ml), NaCl (18 mg/ml), sucrose (3 mg/ml). The eluate contained one major peak at 0.58 column volumes which was collected and contained 348 µg of conjugate (7) in 2.5 ml. The product was characterised by non-reduced SDS PAGE indicating that the band corresponding HC containing the modified glycan was slightly shifted towards higher MW. Also, analytical cyclodextrin-affinity chromatography with and without spiking with wt B-domain deleted FVIII proved that the conjugate bound to cyclodextrin whereas wt B-domain deleted FVIII did not.

Example 12

Preparation of O-Glycan PEGylated/N-Glycan Hydrophobic Side Chain Modified Wt B-Domain Deleted FVIII: Compound 8 wt B-domain deleted FVIII (1 mg, 5.6 nmol) was subjected to a PEGylation reaction using sialidase (*A. ureafaciens*), ST3Gal-1, and 40 kDa PSC (for a description of this compound see WO 2007/056191 A2) as described in WO2009/108806 A1. After completion of the reaction, the product was applied to a SUPERDEX®200 10/300 GL gelfiltration column and eluted with 20 mM imidazole, 10 mM CaCl$_2$, 0.02% TWEEN® 80, 1 M glycerol, pH 7.3, 25 mM NaCl. The product containing the PEGylated FVIII eluted as two partially separated peaks between 0.38 and 0.54 column volumes. This pool was purified by spin column AIEC as outlined in example 9 (omitting step 3) and the final elution was performed with 3×300 µl of buffer 20 mM imidazole, 10 mM CaCl2, 0.02% TWEEN®80, 1 M glycerol, pH 7.3, 1 M NaCl giving the PEGylated FVIII 240 µg in 600 µl. Next, the product was treated with MBP-SBD-ST3Gal-III (125 µl, 0.33 mg/ml, approximately 0.5 U/ml) and substrate 3 (15 µl, 20 nmol). The reaction mixture was incubated at 32° C. for 20 h, after which CMP-NAN (34 mg/ml, 14 µl) was added and allowed to react at 32° C. for 1 h. The reaction mixture was then frozen at −80° C. The thawed sample was diluted with buffer (25 ml of 20 mM imidazole, 10 mM CaCl$_2$, 0.02% TWEEN® 80, 1 M glycerol, pH 7.3) and purified on a spin column AIEC as outlined in example 9. The final elution was performed with 3×250 µl of 20 mM imidazole, 10 mM CaCl$_2$, 0.02% TWEEN® 80, 1 M glycerol, pH 7.3, 1 M NaCl. The pool was applied to a SUPERDEX®200 10/300 GL gelfiltration column and eluted with histidine (1.5 mg/ml), CaCl$_2$ (0.25 mg/ml), TWEEN®80 (0.1 mg/ml), NaCl (18 mg/ml), sucrose (3 mg/ml). The eluate contained one peak at 0.58 column volumes which contained non-PEGylated FVIII and two non-separated peaks around 0.43 column volumes. The early eluting of these two peaks were probably ST3Gal-III (in an aggregated form) while the late eluting peak contained the desired compound. Fractions containing the desired compound (8) with low amount of ST3Gal-III were collected (50 µg in 2.5 ml) and non-reduced SDS PAGE showed that the HC was shifted to higher MW, consistent with the attachment of a PEG to the O-glycan. Non-reduced SDS PAGE with prior thrombin cleavage showed that the bands corresponding to A1 and A3C1C2 containing the modified glycans were shifted towards higher MW, consistent with the attachment of substrate 3 to the N-glycans.

Example 13

Asialo Wt B-Domain Deleted FVIII

Asialo wt B-domain deleted FVIII was obtained through treatment of wt B-domain deleted FVIII with a sialidase, via two routes. The first route included the treatment of wt B-domain deleted FVIII with a sialidase immediately prior to or simultaneously with (one-pot) sialyltransferase mediated coupling of modifying groups to either 0- or N-glycans of FVIII. This is described in examples 8, 11, and 12.

Alternatively, asialo wt B-domain deleted FVIII was obtained in the following way (examples 9 and 10). wt B-domain deleted FVIII was subjected to a PEGylation reaction using sialidase (*A. ureafaciens*), ST3Gal-1, and 40 kDa PSC as described in WO2009/108806 A1. After completion of the reaction, the (un-PEGylated) asialo-FVIII was separated from the PEGylated FVIII by AIEC. Finally, the asialo-FVIII was buffer-exchanged using a MonoQ AIEC column. An amount of 37.4 mg of the asialo-FVIII isolated from the AIEC in 82 ml buffer was diluted with MQ water (150 ml) to obtain a conductivity of 12 mS/cm and was loaded to the column which had been equilibrated with buffer histidine (1.5 mg/ml), $CaCl_2$ (0.25 mg/ml), TWEEN®80 (0.1 mg/ml), NaCl (50 mM), sucrose (3 mg/ml). The product was eluted using a gradient of buffer histidine (1.5 mg/ml), $CaCl_2$ (0.25 mg/ml), TWEEN®80 (0.1 mg/ml), NaCl (1 M), sucrose (3 mg/ml). The product eluted at approximately 500 mM NaCl.

Example 14

Enzymatic Coupling of Substrate 4 to Asialo Transferrin. Preparation of N-Glycan Modified Transferrin Substrate 4 (2.7 mg; 2.0 µmol) was dissolved in 100 µl imidazole buffer (20 mM imidazole, 10 mM $CaCl_2$, 0.02% TWEEN®80, 150 mM NaCl, 1M glycerol pH 7.3) containing 20%(w/v) HPCD. A solution of asialo transferrin (0.4 mg) in 200 µl imidazole buffer, was added followed by MBP-SBD-ST3Gal-III enzyme (0.33 mg/ml) in 20 µl Hepes buffer (14 mM Hepes; 140 mM NaCl, 50% (v/v) glycerol, pH 7.0). To the mixture was added additional imidazole buffer (80 µl) to a total reaction volume of 400 µl, and then incubated for 2 h at room temperature. Reaction mixture was analyzed by LC/MSD TOF (AGILENT® technology), applying deconvolution algorithms on spectra measured at 300-2000 Da. Product distribution was calculated based on peak intensity (yield; m/z): unreacted asialo transferrin (28%; 78386.3869 Da); mono-derivatized asialotransferrin (48%; 79409.8768 Da); double derivatized asialotransferrin (24%; 80440.8368 Da). This example show that it is possible subsequently to obtain analytical data showing the mass of the formed product to verify that the hydrophobic side group of substrate 4 has been transferred to the asialo glycan of a polypeptide (transferrin).

Example 15

Albumin-Binding of FVIII Conjugated with Hydrophobic Side Chain

A SEPHAROSE®-HSA (human serum albumin) column was prepared using a HITRAP® NHS column (GE Healthcare, CV 1 ml, product 17-0716-01) by following the GE Healthcare instruction leaflet 71-7006-00 AT. The substitution was 10 µmol/ml. HSA from Sigma (A1653) was used. An amount of 1 mg in 1 ml buffer was used for coupling. The coupling efficiency was determined to 71% by the protocol described in the above mentioned instruction leaflet.

The column was used with the following conditions:
Flow: 0.5 ml/min
Equilibration buffer: A-buffer: 20 mM imidazole, 10 mM $CaCl_2$, 150 mM NaCl, pH 7.3, 10% glycerol
Elution buffer: B-buffer: 20 mM hydroxypropyl cyclodextrin in A-buffer
Temp: 22° C.
Detection: fluorescence detection, exitation 315 nm, emission: 375 nm A step gradient was used, stepping from 0% to 20% (retention time 3 min) to 60% (5.25 min) to 100% (7.5 min) of B buffer.

Three samples were run in this manner:
1) a blank sample, showing no peaks, but low intensity broad signal corresponding to the hydroxypropyl cyclodextrin step gradient
2) a sample of wt BDD FVIII ("N8"), showing a peak at a retention time of 2.5 min corresponding to the column void volume, thus this protein has no affinity for the column
3) a sample of the crude reaction mixture of an albumin binder FVIII conjugate prepared analogous to compound 6 of example 10, showing a peak at a retention time of 2.5 min corresponding to the column void volume, in addition to a peak with a retention of 7.5 min corresponding to elution at 20% B-buffer. Thus, a fraction of the protein was bound to the column. This fraction was isolated and found to be FVIII modified with the hydrophobic side chain corresponding to compound 6. This was determined by observing a shift in bands corresponding to LC and HC in SDS PAGE analysis.

In a similar experiment it was found that none of the proteins of samples 2 or 3 bound to a column containing no immobilised protein.

This example shows that, under the conditions of the experiment, wt BDD FVIII does not bind to HSA, while the FVIII derivative modified with the hydrophobic side chain corresponding to compound 6 bind to HSA.

Example 16

In Vitro Activity (FVIII:C) Characterisation of FVIII Conjugated with Hydrophobic Side-Chains The FVIII activity (FVIII:C) of the FVIII derivatives 5-8 was evaluated in a chromogenic FVIII assay using COATEST®SP reagents (Chromogenix) as follows: FVIII samples and a FVIII standard (e.g. purified wild-type rFVIII calibrated against the 7th international FVIII standard from NIBSC) were diluted in COATEST® assay buffer (50 mM Tris, 150 mM NaCl, 1% BSA, pH 7.3, with preservative). 50 µl of samples, standards, and buffer negative control were added to 96-well microtiter plates (Nunc) in duplicates. The factor IXa/factor X reagent, the phospholipid reagent and $CaCl_2$ from the COATEST®SP kit were mixed 5:1:3 (vol:vol:vol) and 75 µl of this added to the wells. After 15 min incubation at room temperature 50 μl of the factor Xa substrate S-2765/thrombin inhibitor 1-2581 mix was added and the reactions incubated 10 min at room temperature before 25 μl 1 M citric acid, pH 3, was added. The absorbance at 415 nm was measured on a Spectramax microtiter plate reader (Molecular Devices) with absorbance at 620 nm used as reference wavelength. The value for the negative control was subtracted from all samples and a calibration curve prepared by linear regression of the absorbance values plotted vs. FVIII concentration. The specific activity was calculated by dividing the activity of the samples with the protein concentration determined by HPLC.

TABLE 1

| Conjugate | Modifications | Specific FVIII:C activity (IU/mg) |
| --- | --- | --- |
| 5 (Example 9) | Attachment of substrate 1 to the N-glycans | 6378 |
| 6 (Example 10) | Attachment of substrate 3 to the N-glycans | 5522 |
| 7 (Example 11) | Attachment of substrate 3 to the O-glycan | 6628 |
| 8 (Example 12) | Attachment of substrate 3 to the N-glycans and a 40 kDa PEG to the O-glycan | 4530 |
| wt BDD FVIII ("N8") | — | 9300-10000 |

Example 17

FVIII:C Measured in One-Stage Clot Assay

FVIII:C of the FVIII derivatives 5-8 was further evaluated in a one-stage FVIII clot assay as follows: FVIII derivative samples and a FVIII standard (e.g. purified wild-type rFVIII calibrated against the 7th international FVIII standard from NIBSC) were diluted in HBS/BSA buffer (20 mM hepes, 150 mM NaCl, pH 7.4 with 1% BSA) to approximately 10 U/ml followed by 10-fold dilution in FVIII-deficient plasma containing VWF (Dade Behring). The samples were subsequently diluted in HBS/BSA buffer. The APTT clot time was measured on an ACL300R or an ACL5000 instrument (Instrumentation Laboratory) using the single factor program. FVIII-deficient plasma with VWF (Dade Behring) was used as assay plasma and SYNTHASIL®, (HEMOSIL® Instrumentation Laboratory) as APTT (activated partial thromboplastin time) reagent (e.g., synthetic phospholipids with colloidal silica activator). In the clot instrument, the diluted sample or standard was mixed with FVIII-deficient plasma and aPTT reagents at 37° C. Calcium chloride was added and time until clot formation was determined by turbidity. The FVIII:C in the sample was calculated based on a standard curve of the clot formation times of the dilutions of the FVIII standard. The data in Table 2 demonstrate that the specific FVIII:C activity measured by clot assay of the FVIII derivatives 5-8 was good to excellent.

TABLE 2

| Conjugate | Modifications | Specific FVIII:C one-stage clot activity (IU/mg) |
| --- | --- | --- |
| 5 (Example 9) | Attachment of substrate 1 to the N-glycans | 3522 |
| 6 (Example 10) | Attachment of substrate 3 to the N-glycans | 4165 |
| 7 (Example 11) | Attachment of substrate 3 to the O-glycan | 5766 |
| 8 (Example 12) | Attachment of substrate 3 to the N-glycans and a 40 kDa PEG to the O-glycan | 1750 |
| wt BDD FVIII ("N8") | — | 9300-10000 |

Example 18

Pharmacokinetic Characterisation of FVIII Conjugated with Hydrophobic Side-Chains The phamacokinetics of rFVIII variants were evaluated in FVIII-deficient mice (FVIII exon 16 knock out (KO) mice with C57Bl/6 background, bred at Taconic M&B) or in vWF-deficient mice (vWF exon 4+5 KO mice with C57Bl/6 background bred at Charles River, Germany). The vWF-KO mice had 13% of normal FVIII:C, while the FV111-KO mice had no detectable FVIII:C. A mixture of male and female (approximately 1:1) with an approximate weight of 25 grams and age range of 16-28 weeks were used. The mice received a single i.v. injection of rFVIII (280 IU/kg) in the tail vein. Blood was taken from the orbital plexus at time points up to 64 hours after dosing using non-coated capillary glass tubes. Three samples were taken from each mouse, and 2 to 4 samples were collected at each time point. Blood was immediately stabilized with sodium citrate and diluted in four volumes FVIII COATEST®SP buffer (see example 16) before 5 min centrifugation at 4000×g. Plasma obtained from diluted blood was frozen on dry ice and kept at −80° C. The FVIII:C was determined in a chromogenic assay as described in example 16. Pharmacokinetic analysis was carried out by noncompartmental methods (NCA) using WinNonlin Pro version 4.1 software. Table 2 show estimates for the pharmacokinetic parameters: The half-life (t½), clearance (CL) and mean residence time (MRT). The data show than the clearance was decreased and the half-life and the mean residence time increased upon conjugation of FVIII with hydrophobic side chains.

TABLE 3

| Conjugate | Modifications of the wt BDD FVIII | Species | t½ (h) | MRT (h) | CL (ml/h/kg) |
| --- | --- | --- | --- | --- | --- |
| 5 (Example 9) | Attachment of substrate 1 to the N-glycans | FVIII KO mice | 12 | 15 | 4.5 |
| 6 (Example 10) | Attachment of substrate 3 to the N-glycans | FVIII KO mice | 11 | 14 | 6.6 |
| 7 (Example 11) | Attachment of substrate 3 to the O-glycan | FVIII KO mice | 9.4 | 14 | 4.6 |

TABLE 3-continued

| Conjugate | Modifications of the wt BDD FVIII | Species | t½ (h) | MRT (h) | CL (ml/h/kg) |
|---|---|---|---|---|---|
| 8 (Example 12) | Attachment of substrate 3 to the N-glycans and a 40 kDa PEG to the O-glycan | vWF KO mice | 11 | 15 | 6.6 |
| wt BDD FVIII ("N8") | — | FVIII KO mice | 6.7-9.3 | 9.9-11 | 8.1-10 |
| wt BDD FVIII ("N8") | — | vWF KO mice | 0.5 | 0.64 | 151 |

Example 19

Preparation of N-Glycan Hydrophobic Side Chain Modified FVIIa

The following reagents were used:
Asialo FVIIa (internal batch): in Gly-Gly buffer, pH 6 (1.39 mg/ml), 500 µl, 13 nmol was used Substrate 1 (albumin binder-GSC): (MW 1869): 2 mg/ml, 30 µl or 32 nmol was used. MBP-SBP-ST3Gal-III: 1.2 U/ml, 100 µl was used Asialo-FVIIa referred to a recombinant FVIIa which had been pre-treated with a sialidase and purified. Asialo-FVIIa was thawed, and Substrate 1 and ST3Gal-III were added. The mixture was incubated at 32° C. After 110 min, a sample was separated by cyclodextrin-affinity chromatography. The chromatogram contained two peaks. The first eluting peak corresponded to un-modified asialo-FVIIa and the last eluting peak corresponded to the asialo-FVIIa modified with the albumin binder, as shown by an increase in molecular weight of FVIIa heavy and light chains using SDS-PAGE.

This example shows that modification of FVIIa at its N.glycans with the hydrophobic scide chain of substrate 3 is possible Example 15

Preparation of N-Glycan Hydrophobic Side Chain Modified FIX

The following reagents were used:
FIX (internal batch): in 10 mM histidine, 3 mM CaCl$_2$, 50 mM NaCl buffer pH 6 (11 mg/ml). 100 µl (20 nmol) was diluted to 1 ml with buffer 20 mM imidazole, 10 mM CaCl2, 150 mM NaCl, pH 7.3, 10% glycerol pH 7.3. 100 µl (2 nmol) was used Substrate 1 (albumin binder GSC, MW 1869): 2 mg/ml, 7.5 µl (8 nmol) was used MBP-SBP-ST3Gal-III: 1.2 U/ml, 25 µl was used Sialidase/Neuramidase: 50 µl (6.7 mU) (*C. perfringens*, type VI-A, N-5254 from Sigma) on agarose (suspension), 0.6-1.8 U/ml gel The sialidase was spun down using a PIERCE® spin column and washed twice with water 500 µl, then three times with buffer 50 mM HEPES, 100 mM NaCl, 10 mM CaCl$_2$ pH 7. It was spun down and the enzyme was added to the thawed FIX. The reaction was shaken gently at room temperature overnight and then filtered using a PIERCE® spin column. The resulting filtrate containing asialo FIX was given substrate 1 and ST3Gal-III, and incubated at 32° C. for 46 h. A sample of the reaction mixture was separated by cyclodextrin-affinity chromatography. The chromatogram contained two peaks. The first eluting peak corresponded to un-modified asialo-FIX and the last eluting peak corresponded to the asialo-FIX modified with the albumin binder, as shown by an increase in molecular weight of FVIIa heavy and light chains using SDS-PAGE. The gels also showed the presence of small amounts of FIXa generated by self-activation of FIX.

This example shows that modification of FIX at its N-glycans with the hydrophobic scide chain of substrate 3 is possible

The invention claimed is:
1. A recombinant protein covalently conjugated to at least one hydrophobic side group having the formula:

(A-W-B1-B2)$_z$-asialoProtein wherein:
asialoProtein represents a protein in which the terminal sialic acid has been removed from a glycan;
z represents an integer of the value 1, 2, 3, 4, 5, 6, 7, 8, 9, or 10;
B2 represents a glycyl-sialic acid having the structure

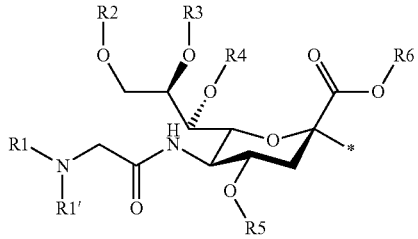

wherein R1, R1', R2, R3, R4, R5, and R6 are either a bond connecting B2 with B1 or a hydrogen and * denotes the connection to asialoProtein;
B1 represents a linker;
W represents a chemical group linking A and B1; and
A represents a hydrophobic albumin binding side group, wherein the side group is derived from substrate 1, 3 or 4;
wherein substrate 1 is

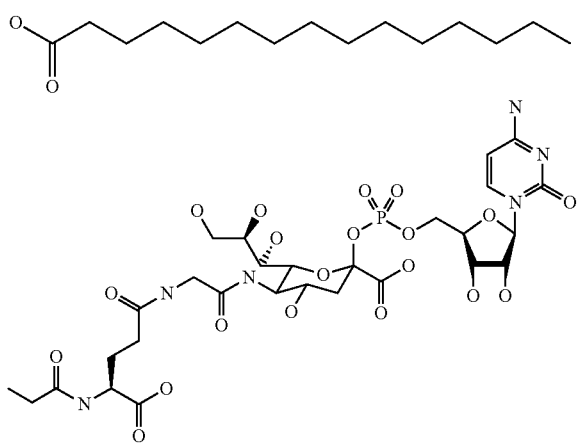

wherein substrate 3 is

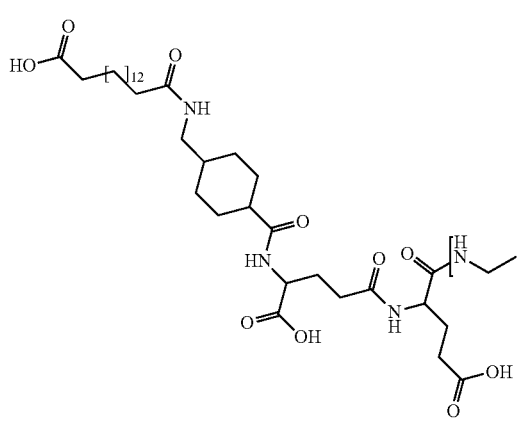

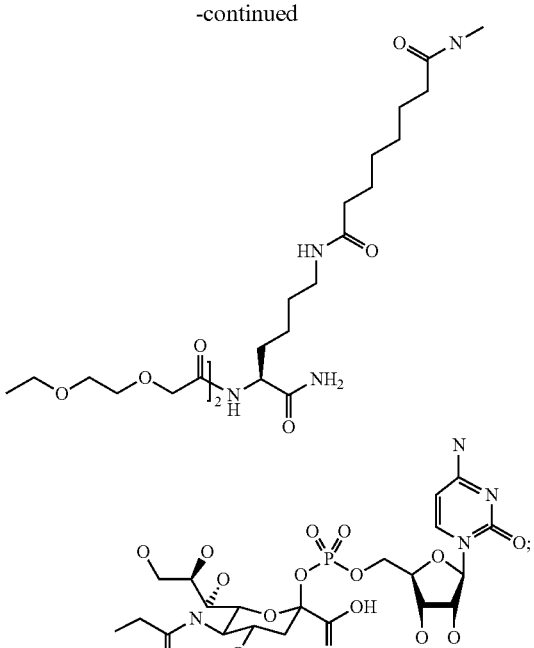

and
wherein substrate 4 is

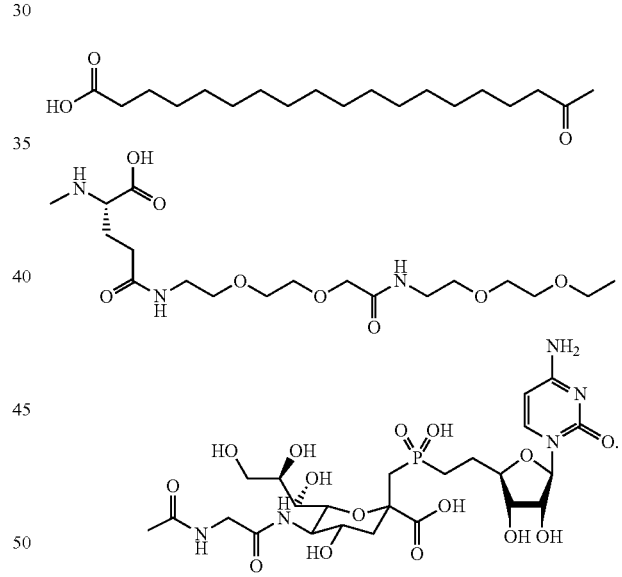

2. The protein according to claim 1, wherein the protein is a coagulation factor.
3. The coagulation factor according to claim 2, wherein the coagulation factor is a Factor VIII (FVIII) molecule.
4. The FVIII molecule according to claim 3, wherein said FVIII molecule has reduced von Willebrand Factor binding capacity.
5. The FVIII molecule according to claim 3, wherein the hydrophobic side group is covalently conjugated to an O-glycan via a sialic acid, wherein said O-glycan is situated in a truncated B-domain, and wherein Factor VIII activation results in removal of said hydrophobic side group.
6. The FVIII molecule according to claim 3, wherein said FVIII molecule is furthermore conjugated with at least one hydrophilic polymer.

7. The coagulation factor according to claim 2, wherein the coagulation factor is a FVII molecule.

8. The coagulation factor according to claim 2, wherein the coagulation factor is a FIX molecule.

9. The recombinant protein according to claim 1, wherein the protein is an antigen binding fragment of an antibody.

10. The recombinant protein according to claim 1, wherein the hydrophobic side group is selected from one or more of the group consisting of: fatty acid and fatty diacid.

11. A pharmaceutical composition comprising a molecule according to claim 1.

12. A method of making a molecule according to claim 1, wherein said method comprises attachment of a hydrophobic side group to a recombinant protein via a sialyltransferase-catalysed reaction.

13. A method of treating an inflammatory disease comprising administering to a subject in need thereof an antigenic binding fragment of an antibody according to claim 9.

14. A method of treating haemophilia comprising administering to a subject in need thereof a molecule according to claim 1.

\* \* \* \* \*

SEQUENCE LISTING

```
<160> NUMBER OF SEQ ID NOS: 4

<210> SEQ ID NO 1
<211> LENGTH: 406
<212> TYPE: PRT
<213> ORGANISM: homo sapiens
<220> FEATURE:
<221> NAME/KEY: X
<222> LOCATION: (6)..(7)
<223> OTHER INFORMATION: X: represents a gamma-carboxylated Glu ("E")
      residue
<220> FEATURE:
<221> NAME/KEY: X
<222> LOCATION: (14)..(14)
<223> OTHER INFORMATION: X: represents a gamma-carboxylated Glu ("E")
      residue
<220> FEATURE:
<221> NAME/KEY: X
<222> LOCATION: (16)..(16)
<223> OTHER INFORMATION: X: represents a gamma-carboxylated Glu ("E")
      residue
<220> FEATURE:
<221> NAME/KEY: X
```

```
<222> LOCATION: (19)..(20)
<223> OTHER INFORMATION: X: represents a gamma-carboxylated Glu ("E")
      residue
<220> FEATURE:
<221> NAME/KEY: X
<222> LOCATION: (25)..(26)
<223> OTHER INFORMATION: X: represents a gamma-carboxylated Glu ("E")
      residue
<220> FEATURE:
<221> NAME/KEY: X
<222> LOCATION: (29)..(29)
<223> OTHER INFORMATION: X: represents a gamma-carboxylated Glu ("E")
      residue
<220> FEATURE:
<221> NAME/KEY: X
<222> LOCATION: (35)..(35)
<223> OTHER INFORMATION: X: represents a gamma-carboxylated Glu ("E")
      residue

<400> SEQUENCE: 1
```

Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser Asp Gly Asp
            35                  40                  45

Gln Cys Ala Ser Ser Pro Cys Gln Asn Gly Gly Ser Cys Lys Asp Gln
50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
            115                 120                 125

Pro Thr Val Glu Tyr Pro Cys Gly Lys Ile Pro Ile Leu Glu Lys Arg
130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
            195                 200                 205

Gly Glu His Asp Leu Ser Glu His Asp Gly Asp Glu Gln Ser Arg Arg
210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
            275                 280                 285

Asp Arg Gly Ala Thr Ala Leu Glu Leu Met Val Leu Asn Val Pro Arg
290                 295                 300

Leu Met Thr Gln Asp Cys Leu Gln Gln Ser Arg Lys Val Gly Asp Ser

```
305                 310                 315                 320
Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
                340                 345                 350

Arg Gly Thr Trp Tyr Leu Thr Gly Ile Val Ser Trp Gly Gln Gly Cys
                355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405

<210> SEQ ID NO 2
<211> LENGTH: 2332
<212> TYPE: PRT
<213> ORGANISM: homo sapiens

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
                180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270
```

```
Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asn Ser Pro Ser Phe
    355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
```

-continued

```
            690             695             700
Leu Leu Lys Val Ser Ser Cys Asp Lys Asn Thr Gly Asp Tyr Tyr Glu
705             710             715             720

Asp Ser Tyr Glu Asp Ile Ser Ala Tyr Leu Ser Lys Asn Asn Ala
            725             730             735

Ile Glu Pro Arg Ser Phe Ser Gln Asn Ser Arg His Pro Ser Thr Arg
            740             745             750

Gln Lys Gln Phe Asn Ala Thr Thr Ile Pro Glu Asn Asp Ile Glu Lys
            755             760             765

Thr Asp Pro Trp Phe Ala His Arg Thr Pro Met Pro Lys Ile Gln Asn
            770             775             780

Val Ser Ser Ser Asp Leu Leu Met Leu Leu Arg Gln Ser Pro Thr Pro
785             790             795             800

His Gly Leu Ser Leu Ser Asp Leu Gln Glu Ala Lys Tyr Glu Thr Phe
            805             810             815

Ser Asp Asp Pro Ser Pro Gly Ala Ile Asp Ser Asn Asn Ser Leu Ser
            820             825             830

Glu Met Thr His Phe Arg Pro Gln Leu His His Ser Gly Asp Met Val
            835             840             845

Phe Thr Pro Glu Ser Gly Leu Gln Leu Arg Leu Asn Glu Lys Leu Gly
850             855             860

Thr Thr Ala Ala Thr Glu Leu Lys Lys Leu Asp Phe Lys Val Ser Ser
865             870             875             880

Thr Ser Asn Asn Leu Ile Ser Thr Ile Pro Ser Asp Asn Leu Ala Ala
            885             890             895

Gly Thr Asp Asn Thr Ser Ser Leu Gly Pro Pro Ser Met Pro Val His
            900             905             910

Tyr Asp Ser Gln Leu Asp Thr Thr Leu Phe Gly Lys Lys Ser Ser Pro
            915             920             925

Leu Thr Glu Ser Gly Gly Pro Leu Ser Leu Ser Glu Glu Asn Asn Asp
930             935             940

Ser Lys Leu Leu Glu Ser Gly Leu Met Asn Ser Gln Glu Ser Ser Trp
945             950             955             960

Gly Lys Asn Val Ser Ser Thr Glu Ser Gly Arg Leu Phe Lys Gly Lys
            965             970             975

Arg Ala His Gly Pro Ala Leu Leu Thr Lys Asp Asn Ala Leu Phe Lys
            980             985             990

Val Ser Ile Ser Leu Leu Lys Thr Asn Lys Thr Ser Asn Asn Ser Ala
            995             1000            1005

Thr Asn Arg Lys Thr His Ile Asp Gly Pro Ser Leu Leu Ile Glu
            1010            1015            1020

Asn Ser Pro Ser Val Trp Gln Asn Ile Leu Glu Ser Asp Thr Glu
            1025            1030            1035

Phe Lys Lys Val Thr Pro Leu Ile His Asp Arg Met Leu Met Asp
            1040            1045            1050

Lys Asn Ala Thr Ala Leu Arg Leu Asn His Met Ser Asn Lys Thr
            1055            1060            1065

Thr Ser Ser Lys Asn Met Glu Met Val Gln Gln Lys Lys Glu Gly
            1070            1075            1080

Pro Ile Pro Pro Asp Ala Gln Asn Pro Asp Met Ser Phe Phe Lys
            1085            1090            1095

Met Leu Phe Leu Pro Glu Ser Ala Arg Trp Ile Gln Arg Thr His
            1100            1105            1110
```

-continued

Gly Lys Asn Ser Leu Asn Ser Gly Gln Gly Pro Ser Pro Lys Gln
1115                 1120                1125

Leu Val Ser Leu Gly Pro Glu Lys Ser Val Glu Gly Gln Asn Phe
1130                 1135                1140

Leu Ser Glu Lys Asn Lys Val Val Val Gly Lys Gly Glu Phe Thr
1145                 1150                1155

Lys Asp Val Gly Leu Lys Glu Met Val Phe Pro Ser Ser Arg Asn
1160                 1165                1170

Leu Phe Leu Thr Asn Leu Asp Asn Leu His Glu Asn Asn Thr His
1175                 1180                1185

Asn Gln Glu Lys Lys Ile Gln Glu Glu Ile Glu Lys Lys Glu Thr
1190                 1195                1200

Leu Ile Gln Glu Asn Val Val Leu Pro Gln Ile His Thr Val Thr
1205                 1210                1215

Gly Thr Lys Asn Phe Met Lys Asn Leu Phe Leu Leu Ser Thr Arg
1220                 1225                1230

Gln Asn Val Glu Gly Ser Tyr Asp Gly Ala Tyr Ala Pro Val Leu
1235                 1240                1245

Gln Asp Phe Arg Ser Leu Asn Asp Ser Thr Asn Arg Thr Lys Lys
1250                 1255                1260

His Thr Ala His Phe Ser Lys Lys Gly Glu Glu Glu Asn Leu Glu
1265                 1270                1275

Gly Leu Gly Asn Gln Thr Lys Gln Ile Val Glu Lys Tyr Ala Cys
1280                 1285                1290

Thr Thr Arg Ile Ser Pro Asn Thr Ser Gln Gln Asn Phe Val Thr
1295                 1300                1305

Gln Arg Ser Lys Arg Ala Leu Lys Gln Phe Arg Leu Pro Leu Glu
1310                 1315                1320

Glu Thr Glu Leu Glu Lys Arg Ile Ile Val Asp Asp Thr Ser Thr
1325                 1330                1335

Gln Trp Ser Lys Asn Met Lys His Leu Thr Pro Ser Thr Leu Thr
1340                 1345                1350

Gln Ile Asp Tyr Asn Glu Lys Glu Lys Gly Ala Ile Thr Gln Ser
1355                 1360                1365

Pro Leu Ser Asp Cys Leu Thr Arg Ser His Ser Ile Pro Gln Ala
1370                 1375                1380

Asn Arg Ser Pro Leu Pro Ile Ala Lys Val Ser Ser Phe Pro Ser
1385                 1390                1395

Ile Arg Pro Ile Tyr Leu Thr Arg Val Leu Phe Gln Asp Asn Ser
1400                 1405                1410

Ser His Leu Pro Ala Ala Ser Tyr Arg Lys Lys Asp Ser Gly Val
1415                 1420                1425

Gln Glu Ser Ser His Phe Leu Gln Gly Ala Lys Lys Asn Asn Leu
1430                 1435                1440

Ser Leu Ala Ile Leu Thr Leu Glu Met Thr Gly Asp Gln Arg Glu
1445                 1450                1455

Val Gly Ser Leu Gly Thr Ser Ala Thr Asn Ser Val Thr Tyr Lys
1460                 1465                1470

Lys Val Glu Asn Thr Val Leu Pro Lys Pro Asp Leu Pro Lys Thr
1475                 1480                1485

Ser Gly Lys Val Glu Leu Leu Pro Lys Val His Ile Tyr Gln Lys
1490                 1495                1500

-continued

Asp Leu Phe Pro Thr Glu Thr Ser Asn Gly Ser Pro Gly His Leu
1505              1510               1515

Asp Leu Val Glu Gly Ser Leu Leu Gln Gly Thr Glu Gly Ala Ile
1520              1525               1530

Lys Trp Asn Glu Ala Asn Arg Pro Gly Lys Val Pro Phe Leu Arg
1535              1540               1545

Val Ala Thr Glu Ser Ser Ala Lys Thr Pro Ser Lys Leu Leu Asp
1550              1555               1560

Pro Leu Ala Trp Asp Asn His Tyr Gly Thr Gln Ile Pro Lys Glu
1565              1570               1575

Glu Trp Lys Ser Gln Glu Lys Ser Pro Glu Lys Thr Ala Phe Lys
1580              1585               1590

Lys Lys Asp Thr Ile Leu Ser Leu Asn Ala Cys Glu Ser Asn His
1595              1600               1605

Ala Ile Ala Ala Ile Asn Glu Gly Gln Asn Lys Pro Glu Ile Glu
1610              1615               1620

Val Thr Trp Ala Lys Gln Gly Arg Thr Glu Arg Leu Cys Ser Gln
1625              1630               1635

Asn Pro Pro Val Leu Lys Arg His Gln Arg Glu Ile Thr Arg Thr
1640              1645               1650

Thr Leu Gln Ser Asp Gln Glu Glu Ile Asp Tyr Asp Asp Thr Ile
1655              1660               1665

Ser Val Glu Met Lys Lys Glu Asp Phe Asp Ile Tyr Asp Glu Asp
1670              1675               1680

Glu Asn Gln Ser Pro Arg Ser Phe Gln Lys Lys Thr Arg His Tyr
1685              1690               1695

Phe Ile Ala Ala Val Glu Arg Leu Trp Asp Tyr Gly Met Ser Ser
1700              1705               1710

Ser Pro His Val Leu Arg Asn Arg Ala Gln Ser Gly Ser Val Pro
1715              1720               1725

Gln Phe Lys Lys Val Val Phe Gln Glu Phe Thr Asp Gly Ser Phe
1730              1735               1740

Thr Gln Pro Leu Tyr Arg Gly Glu Leu Asn Glu His Leu Gly Leu
1745              1750               1755

Leu Gly Pro Tyr Ile Arg Ala Glu Val Glu Asp Asn Ile Met Val
1760              1765               1770

Thr Phe Arg Asn Gln Ala Ser Arg Pro Tyr Ser Phe Tyr Ser Ser
1775              1780               1785

Leu Ile Ser Tyr Glu Glu Asp Gln Arg Gln Gly Ala Glu Pro Arg
1790              1795               1800

Lys Asn Phe Val Lys Pro Asn Glu Thr Lys Thr Tyr Phe Trp Lys
1805              1810               1815

Val Gln His His Met Ala Pro Thr Lys Asp Glu Phe Asp Cys Lys
1820              1825               1830

Ala Trp Ala Tyr Phe Ser Asp Val Asp Leu Glu Lys Asp Val His
1835              1840               1845

Ser Gly Leu Ile Gly Pro Leu Leu Val Cys His Thr Asn Thr Leu
1850              1855               1860

Asn Pro Ala His Gly Arg Gln Val Thr Val Gln Glu Phe Ala Leu
1865              1870               1875

Phe Phe Thr Ile Phe Asp Glu Thr Lys Ser Trp Tyr Phe Thr Glu
1880              1885               1890

Asn Met Glu Arg Asn Cys Arg Ala Pro Cys Asn Ile Gln Met Glu

-continued

```
            1895                1900                1905
Asp Pro Thr Phe Lys Glu Asn Tyr Arg Phe His Ala Ile Asn Gly
        1910                1915                1920
Tyr Ile Met Asp Thr Leu Pro Gly Leu Val Met Ala Gln Asp Gln
        1925                1930                1935
Arg Ile Arg Trp Tyr Leu Leu Ser Met Gly Ser Asn Glu Asn Ile
        1940                1945                1950
His Ser Ile His Phe Ser Gly His Val Phe Thr Val Arg Lys Lys
        1955                1960                1965
Glu Glu Tyr Lys Met Ala Leu Tyr Asn Leu Tyr Pro Gly Val Phe
        1970                1975                1980
Glu Thr Val Glu Met Leu Pro Ser Lys Ala Gly Ile Trp Arg Val
        1985                1990                1995
Glu Cys Leu Ile Gly Glu His Leu His Ala Gly Met Ser Thr Leu
        2000                2005                2010
Phe Leu Val Tyr Ser Asn Lys Cys Gln Thr Pro Leu Gly Met Ala
        2015                2020                2025
Ser Gly His Ile Arg Asp Phe Gln Ile Thr Ala Ser Gly Gln Tyr
        2030                2035                2040
Gly Gln Trp Ala Pro Lys Leu Ala Arg Leu His Tyr Ser Gly Ser
        2045                2050                2055
Ile Asn Ala Trp Ser Thr Lys Glu Pro Phe Ser Trp Ile Lys Val
        2060                2065                2070
Asp Leu Leu Ala Pro Met Ile Ile His Gly Ile Lys Thr Gln Gly
        2075                2080                2085
Ala Arg Gln Lys Phe Ser Ser Leu Tyr Ile Ser Gln Phe Ile Ile
        2090                2095                2100
Met Tyr Ser Leu Asp Gly Lys Lys Trp Gln Thr Tyr Arg Gly Asn
        2105                2110                2115
Ser Thr Gly Thr Leu Met Val Phe Phe Gly Asn Val Asp Ser Ser
        2120                2125                2130
Gly Ile Lys His Asn Ile Phe Asn Pro Pro Ile Ile Ala Arg Tyr
        2135                2140                2145
Ile Arg Leu His Pro Thr His Tyr Ser Ile Arg Ser Thr Leu Arg
        2150                2155                2160
Met Glu Leu Met Gly Cys Asp Leu Asn Ser Cys Ser Met Pro Leu
        2165                2170                2175
Gly Met Glu Ser Lys Ala Ile Ser Asp Ala Gln Ile Thr Ala Ser
        2180                2185                2190
Ser Tyr Phe Thr Asn Met Phe Ala Thr Trp Ser Pro Ser Lys Ala
        2195                2200                2205
Arg Leu His Leu Gln Gly Arg Ser Asn Ala Trp Arg Pro Gln Val
        2210                2215                2220
Asn Asn Pro Lys Glu Trp Leu Gln Val Asp Phe Gln Lys Thr Met
        2225                2230                2235
Lys Val Thr Gly Val Thr Thr Gln Gly Val Lys Ser Leu Leu Thr
        2240                2245                2250
Ser Met Tyr Val Lys Glu Phe Leu Ile Ser Ser Ser Gln Asp Gly
        2255                2260                2265
His Gln Trp Thr Leu Phe Phe Gln Asn Gly Lys Val Lys Val Phe
        2270                2275                2280
Gln Gly Asn Gln Asp Ser Phe Thr Pro Val Val Asn Ser Leu Asp
        2285                2290                2295
```

-continued

```
Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330

<210> SEQ ID NO 3
<211> LENGTH: 415
<212> TYPE: PRT
<213> ORGANISM: homo sapiens
<220> FEATURE:
<221> NAME/KEY: X
<222> LOCATION: (7)..(8)
<223> OTHER INFORMATION: X: Represents a gamma-carboxylated Glu ("E")
      residue.
<220> FEATURE:
<221> NAME/KEY: X
<222> LOCATION: (15)..(15)
<223> OTHER INFORMATION: X: Represents a gamma-carboxylated Glu ("E")
      residue.
<220> FEATURE:
<221> NAME/KEY: X
<222> LOCATION: (17)..(17)
<223> OTHER INFORMATION: X: Represents a gamma-carboxylated Glu ("E")
      residue.
<220> FEATURE:
<221> NAME/KEY: X
<222> LOCATION: (20)..(21)
<223> OTHER INFORMATION: X: Represents a gamma-carboxylated Glu ("E")
      residue.
<220> FEATURE:
<221> NAME/KEY: X
<222> LOCATION: (26)..(27)
<223> OTHER INFORMATION: X: Represents a gamma-carboxylated Glu ("E")
      residue.
<220> FEATURE:
<221> NAME/KEY: X
<222> LOCATION: (30)..(30)
<223> OTHER INFORMATION: X: Represents a gamma-carboxylated Glu ("E")
      residue.
<220> FEATURE:
<221> NAME/KEY: X
<222> LOCATION: (33)..(33)
<223> OTHER INFORMATION: X: Represents a gamma-carboxylated Glu ("E")
      residue.
<220> FEATURE:
<221> NAME/KEY: X
<222> LOCATION: (36)..(36)
<223> OTHER INFORMATION: X: Represents a gamma-carboxylated Glu ("E")
      residue.
<220> FEATURE:
<221> NAME/KEY: misc_feature
<222> LOCATION: (40)..(40)
<223> OTHER INFORMATION: Xaa can be any naturally occurring amino acid

<400> SEQUENCE: 3

Tyr Asn Ser Gly Lys Leu Xaa Xaa Phe Val Gln Gly Asn Leu Xaa Arg
1               5                   10                  15

Xaa Cys Met Xaa Xaa Lys Cys Ser Phe Xaa Xaa Ala Arg Xaa Val Phe
                20                  25                  30

Xaa Asn Thr Xaa Arg Thr Thr Xaa Phe Trp Lys Gln Tyr Val Asp Gly
            35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95
```

Gln Phe Cys Lys Asn Ser Ala Asp Asn Lys Val Val Cys Ser Cys Thr
                100                 105                 110

Glu Gly Tyr Arg Leu Ala Glu Asn Gln Lys Ser Cys Glu Pro Ala Val
            115                 120                 125

Pro Phe Pro Cys Gly Arg Val Ser Val Ser Gln Thr Ser Lys Leu Thr
        130                 135                 140

Arg Ala Glu Ala Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 4
<211> LENGTH: 21
<212> TYPE: PRT
<213> ORGANISM: artificial
<220> FEATURE:
<223> OTHER INFORMATION: FVIII B domain linker of 21 amino acids

<400> SEQUENCE: 4

Ser Phe Ser Gln Asn Ser Arg His Pro Ser Gln Asn Pro Pro Val Leu
1               5                   10                  15

Lys Arg His Gln Arg
            20